(12) United States Patent
Bachand et al.

(10) Patent No.: US 7,501,419 B2
(45) Date of Patent: Mar. 10, 2009

(54) 4-SQUARYLPIPERAZINE DERIVATIVES AS ANTIVIRAL AGENTS

(75) Inventors: Carol Bachand, Candiac (CA); Daniel H. Deon, Brossard (CA); Edward H. Ruediger, Greenfield Park (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/737,354

(22) Filed: Apr. 19, 2007

(65) Prior Publication Data

US 2007/0249624 A1    Oct. 25, 2007

Related U.S. Application Data

(60) Provisional application No. 60/794,699, filed on Apr. 25, 2006.

(51) Int. Cl.
A61K 31/496 (2006.01)
C07D 295/192 (2006.01)
C07D 403/12 (2006.01)
C07D 405/12 (2006.01)
C07D 487/04 (2006.01)

(52) U.S. Cl. ............... 514/253.04; 514/254.09; 544/230; 544/362; 544/373

(58) Field of Classification Search ............ None
See application file for complete search history.

(56) References Cited

U.S. PATENT DOCUMENTS

| 2005/0209246 A1 | 9/2005 | Ueda et al. |
| 2005/0215543 A1 | 9/2005 | Lin et al. |
| 2005/0215544 A1 | 9/2005 | Lin et al. |
| 2005/0215545 A1 | 9/2005 | Lin et al. |

FOREIGN PATENT DOCUMENTS

| WO | WO 03/103607 A2 | 12/2003 |
| WO | WO 2005/016344 A1 | 2/2005 |
| WO | WO 2005/090367 A1 | 9/2005 |
| WO | WO 2005/121094 A1 | 12/2005 |

OTHER PUBLICATIONS

Drug Evaluations by American Medical Association (6th Ed.), pp. 1615-1627 (1986).*

Blair, et al., "HIV-1 entry—an expanding portal for drug discovery," Drug Discovery Today, vol. 5, Nov. 5, May 2000, pp. 183-194.

Hotoda, "Small-molecule inhibitors of HIV-1 entry via chemokine receptors," Drugs of the Future, 1999, 24(12), pp. 1355-1362.

Liebeskind, L.S., "An Improved Method for the Synthesis of Substituted Cyclobutenediones," J. Org. Chem., 1988, 53, pp. 2482-2488.

Liebeskind, L.S., "Preparation of 3-Acyl-3-cyclobutene-1,2-diones and Some Related Monoacetals," J. Org. Chem., 1993, 58, pp. 3543-3549.

Meanwell, N.A., "Inhibitors of the entry of HIV into host cells," Current Opinion in Drug Discovery and Development, 2003, 6(4), pp. 451-461.

Sodroski, "HIV-1 Entry Inhibitors in the Side Pocket," Cell, vol. 99, Oct. 29, 1999, pp. 243-246.

Want, et al., "Modification and structure-activity relationship of a small molecule HIV-1 inhibitor targeting the viral envelope glycoprotein gp120," Org. Bio. Chem., 2005, 3, pp. 1781-1786.

* cited by examiner

*Primary Examiner*—Emily Bernhardt
(74) *Attorney, Agent, or Firm*—John F. Levis; Jennifer Chin Chapman

(57) ABSTRACT

This disclosure provides compounds having drug and bio-affecting properties, their pharmaceutical compositions and method of use. In particular, the disclosure is concerned with 4-squarylpiperazine derivatives that possess unique antiviral activity. More particularly, the present disclosure relates to compounds useful for the treatment of HIV and AIDS having the following formula:

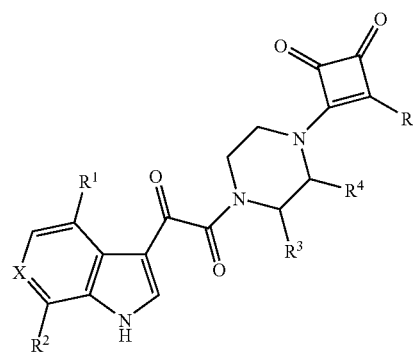

7 Claims, No Drawings

4-SQUARYLPIPERAZINE DERIVATIVES AS ANTIVIRAL AGENTS

CROSS-REFERENCE TO RELATED APPLICATIONS

This application claims the benefit of U.S. Provisional Application Ser. No. 60/794,699 filed Apr. 25, 2006.

FIELD OF THE DISCLOSURE

This disclosure provides compounds having drug and bio-affecting properties, their pharmaceutical compositions and method of use. In particular, the disclosure is concerned with 4-squarylpiperazine derivatives that possess unique antiviral activity. More particularly, the present disclosure relates to compounds useful for the treatment of HIV and AIDS.

BACKGROUND ART

HIV-1 (human immunodeficiency virus-1) infection remains a major medical problem, with an estimated 40 million people infected worldwide at the end of 2005. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), emtricitabine (or FTC), Combivir® (contains −3TC plus AZT), Trizivir® (contains abacavir, lamivudine, and zidovudine), Epzicom® (contains abacavir and lamivudine), Truvada® (contains Viread® and emtricitabine); non-nucleoside reverse transcriptase inhibitors: nevirapine (or Viramune®), delavirdine (or Rescriptor®) and efavirenz (or Sustiva®), and peptidomimetic protease inhibitors or approved formulations: saquinavir, indinavir, ritonavir, nelfinavir, amprenavir, lopinavir, and Kaletra® (lopinavir and Ritonavir). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents currently being studied by a number of investigators.

The properties of a class of HIV entry inhibitors called HIV attachment inhibitors has been improved in an effort to obtain compounds with maximized utility and efficacy as antiviral agents. A disclosure describing indoles of which the structure shown below for BMS-705 is representative has been disclosed [Antiviral Indoleoxoacetyl Piperazine Derivatives].

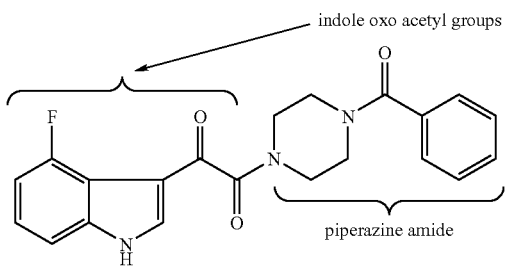

BMS-705

Two other compounds, referred to in the literature as BMS-806 and BMS-043 have been described in both the academic and patent art:

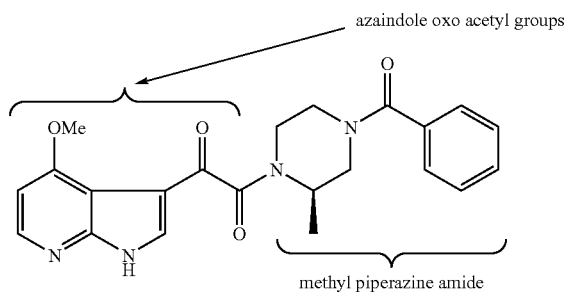

BMS-806

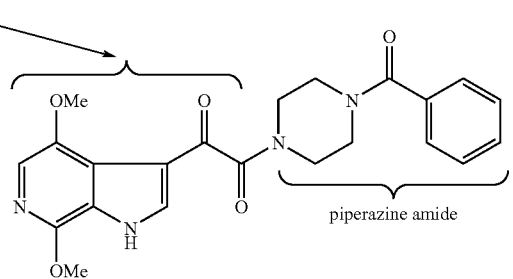

BMS-043

Some description of their properties in human clinical trials have been disclosed in literature.

It should be noted that in all three of these structures, a piperazine amide (In these three structures a piperazine phenyl amide) is present and this group is directly attached to an oxoacetyl moiety. The oxoacetyl group is attached at the 3-position of 4-Fluoro indole in BMS-705 and to the 3 position of substituted azaindoles in BMS-806 and BMS-043.

In an effort to obtain improved anti-HIV compounds, later publications described in part, modified substitution patterns on the indoles and azaindoles. Examples of such effort include: (1) novel substituted indoleoxoacetic piperazine derivatives, (2) substituted piperazinyloxoacetylindole derivatives, and (3) substituted azaindoleoxoacetic piperazine derivatives.

Replacement of these groups with other heteraromatics or substituted heteroaromatics or bicyclic hydrocarbons was also shown to be feasible. Examples include: (1) indole, azaindole and related heterocyclic amidopiperazine derivatives; (2) bicyclo 4.4.0 antiviral derivatives; and (3) diazaindole derivatives.

A select few replacements for the piperazine amide portion of the molecules have also been described in the art and among these examples are (1) some piperidine alkenes; (2) some pyrrolidine amides; (3) some N-aryl or heteroaryl piperazines; (4) some piperazinyl ureas; and (5) some carboline containing compounds.

Method(s) for preparing prodrugs for this class of compounds was disclosed in Prodrugs of Piperazine and Substituted Piperidine Antiviral Agents (Ueda et al., U.S. non-provisional application Ser. No. 11/066,745, filed Feb. 25, 2005 or US20050209246A1 or WO2005090367A1).

A published PCT patent application WO2003103607A1 (Jun. 11, 2003) disclosures an assay useful for assaying some HIV inhibitors.

Several published patent applications describe combination studies with piperazine benzamide inhibitors, for example, US20050215543 (WO2005102328A1), US20050215544 (WO2005102391A1), and US20050215545 (WO2005102392A2).

A publication on new compounds in this class of attachment inhibitors (Jinsong Wang et. al. Org. Biol. Chem. 2005, 3, 1781-1786.) and a patent application on some more remotely related compounds have appeared WO2005/016344 published on Feb. 24, 2005.

Published patent applications WO2005/016344 and WO2005/121094 also describe piperazine derivatives which are HIV inhibitors. The compounds described in these applications are structurally distinct from the compounds of the present disclosure.

Nothing in these references can be construed to disclose or suggest the novel compounds of this disclosure and their use to inhibit HIV infection.

SUMMARY OF THE DISCLOSURE

The present disclosure relates to compounds of Formula I, the pharmaceutically acceptable salts and/or solvates (e.g., hydrates) thereof, their pharmaceutical formulations, and their use in patients suffering from or susceptible to a virus such as HIV. The compounds of Formula I, their pharmaceutically acceptable salts and/or solvate are effective anticiral agents, particularly as inhibitors of HIV. They are useful for the treatment of HIV and AIDS.

One embodiment of the disclosure relates to a compound of Formula I, or pharmaceutically acceptable salts thereof,

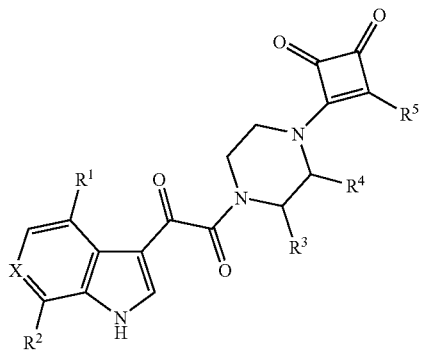

wherein: X is CH or N;

$R^1$ is F or methoxy;

$R^2$ is methoxy, Cl, Br, or heteroaryl wherein said heteroaryl is optionally substituted with one or two of the same or different members selected from the group consisting of amino, nitro, cyano, hydroxy, $C_{1-6}$ alkoxy, —C(O)NH$_2$, $C_{1-6}$ alkyl, —NHC(O)CH$_3$, halogen, and trifluoromethyl;

$R^3$ is H or methyl;

$R^4$ is H or methyl;

$R^5$ is alkyl, aryl, heteroaryl, OR$^6$, or NR$^6$R$^7$;

$R^6$ and $R^7$ are each independently selected from the group consisting of H, $C_1$-$C_6$ alkyl and $C_3$-$C_6$ cycloalkyl, wherein said $C_3$-$C_6$ cycloalkyl can fuse with phenyl or pyridine; $R^6$ and $R^7$ can optional be joined by C, O, N, S or atom, among which the junctioning C and N atom can be substituted with $C_1$-$C_6$ alkyl, $C_3$-$C_6$ cycloalkyl group or junctioning C atom can be a part of $C_3$-$C_6$ cycloalkyl group.

Another embodiment of the present disclosure is a method for treating mammals infected with a virus, especially wherein said virus is HIV, comprising administering to said mammal an antiviral effective amount of a compound of Formula I, and one or more pharmaceutically acceptable carriers, excipients or diluents. Optionally, the compound of Formula I can be administered in combination with an antiviral effective amount of an AIDS treatment agent selected from the group consisting of: (a) an AIDS antiviral agent; (b) an anti-infective agent; (c) an immunomodulator; and (d) HIV entry inhibitors.

Another embodiment of the present disclosure is a pharmaceutical composition comprising an antiviral effective amount of a compound of Formula I and one or more pharmaceutically acceptable carriers, excipients, diluents and optionally in combination with an antiviral effective amount of an AIDS treatment agent selected from the group consisting of: (a) an AIDS antiviral agent; (b) an anti-infective agent; (c) an immunomodulator; and (d) HIV entry inhibitors.

DETAILED DESCRIPTION OF THE DISCLOSURE

Since the compounds of the present disclosure, may possess asymmetric centers and therefore occur as mixtures of diastereomers and enantiomers, the present disclosure includes the individual diastereoisomeric and enantiomeric forms of the compounds of Formula I in addition to the mixtures thereof.

Definitions

The term "$C_{1-6}$alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"Halogen" refers to chlorine, bromine, iodine or fluorine.

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl, diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encomplish systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo-methanesulfonamido, trihalomethanesulfonyl, silyl, guanyl, guanidino, ureido, phosphonyl, amino and —$NR^xR^y$ with $R^x$ and $R^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroaliacyclic group.

A "trihalomethanecarbonyl" group refers to a $Z_3CC(=O)$— group with said Z being a halogen.

A "C-carboxy" group refers to a —C(=O)O—R" groups, with R" as defined herein.

An "O-carboxy" group refers to a R"C(—O)O— group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3CS(=O)_2$— groups with Z as defined above.

A "trihalomethanesulfonamido" group refers to a $Z_3CS(=O)_2NR^x$— group with Z as defined above and $R^x$ being H or $(C_{1-6})$alkyl.

A "sulfinyl" group refers to a —S(=O)—R" group, with R" being $(C_{1-6})$alkyl.

A "sulfonyl" group refers to a —$S(=O)_2R$" group with R" being $(C_{1-6})$alkyl.

A "S-sulfonamido" group refers to a —$S(=O)_2NR^XR^Y$, with $R^X$ and $R^Y$ independently being H or $(C_{1-6})$alkyl.

A "N-Sulfonamido" group refers to a R"$S(=O)_2NR_x$— group, with $R_x$ being H or $(C_{1-6})$alkyl;

A "O-carbamyl" group refers to a —OC(=O)$NR^xR^y$ group, with $R^X$ and $R^Y$ independently being H or $(C_{1-6})$alkyl.

A "N-carbamyl" group refers to a $R^xOC(=O)NR^y$ group, with $R^x$ and $R^y$ independently being H or $(C_{1-6})$alkyl.

A "O-thiocarbamyl" group refers to a —OC(=S)$NR^xR^y$ group, with $R^x$ and $R^y$ independently being H or $(C_{1-6})$alkyl.

A "N-thiocarbamyl" group refers to a $R^xOC(=S)NR^y$— group, with $R^{x1\ and\ Ry}$ independently being H or $(C_{1-6})$alkyl.

An "amino" group refers to an —$NH_2$ group.

A "C-amido" group refers to a —C(=O)$NR^xR^y$ group, with $R^x$ and $R^y$ independently being H or $(C_{1-6})$alkyl.

A "C-thioamido" group refers to a —C(=S)$NR^xR^y$ group, with $R^x$ and $R^y$ independently being H or $(C_{1-6})$alkyl.

A "N-amido" group refers to a $R^xC(=O)NR^y$— group, with $R^x$ and $R^y$ independently being H or $(C_{1-6})$alkyl.

An "ureido" group refers to a —$NR^xC(=O)NR^yR^{y2}$ group, with $R^x$, $R^y$, and $R^{y2}$ independently being H or $(C_{1-6})$alkyl.

A "guanidino" group refers to a —$R^xNC(=N)NR^yR^{y2}$ group, with $R^x$, $R^y$, and $R^{y2}$ independently being H or $(C_{1-6})$alkyl.

A "guanyl" group refers to a $R^xR^yNC(=N)$— group, with $R^x$ and $R^y$ independently being H or $(C_{1-6})$alkyl.

A "cyano" group refers to a —CN group.

A "silyl" group refers to a —$Si(R")_3$, with R" being $(C_{1-6})$ alkyl or phenyl.

A "phosphonyl" group refers to a $P(=O)(OR^x)_2$ with $R^x$ being $(C_{1-6})$alkyl.

A "hydrazino" group refers to a —$NR^xNR^yR^{y2}$ group, with $R^x$, $R^y$, and $R^{y2}$ independently being H or $(C_{1-6})$alkyl.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Physiologically acceptable salts and prodrugs of compounds disclosed herein are within the scope of this disclosure. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris (hydroxymethyl)-aminomethane), or with bases such as piperidine or morpholine.

In the method of the present disclosure, the term "antiviral effective amount" means the total amount of each active component of the method that is sufficient to show a meaningful patient benefit, i.e., healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with HIV infection.

The present disclosure is also directed to combinations of the compounds with one or more agents useful in the treatment of AIDS. For example, the compounds of this disclosure may be effectively administered, whether at periods of pre-exposure and/or post-exposure, in combination with effective amounts of the AIDS antivirals, immunomodulators, antiinfectives, or vaccines, such as those in the following table.

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |

-continued

| Drug Name | Manufacturer | Indication |
|---|---|---|
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, Sustiva ®) (−)6-Chloro-4-(S)-cyclopropylethynyl-4(S)-trifluoromethyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffman-LaRoche | HIV infection, AIDS, ARC, with AZT |
| Zidovudine; AZT | Glaxo Wellcome | HIV infection, AIDS, ARC, Kaposi's sarcoma, in combination with other therapies |

-continued

| Drug Name | Manufacturer | Indication |
|---|---|---|
| Tenofovir disoproxil, fumarate salt (Viread ®) | Gilead | HIV infection, AIDS, (reverse transcriptase inhibitor) |
| Emtriva ® (Emtricitabine) | Gilead | HIV infection, AIDS, (reverse transcriptase inhibitor) |
| Combivir ® | GSK | HIV infection, AIDS, (reverse transcriptase inhibitor) |
| Abacavir succinate (or Ziagen ®) | GSK | HIV infection, AIDS, (reverse transcriptase inhibitor) |
| Reyataz ® (or atazanavir) | Bristol-Myers Squibb | HIV infection AIDs, protease inhibitor |
| Fuzeon ® (or T-20) | Roche/Trimeris | HIV infection AIDs, viral Fusion inhibitor |
| Lexiva ® (or Fosamprenavir calcium) | GSK/Vertex | HIV infection AIDs, viral protease inhibitor |
| Maraviroc; (UK 427857) | Pfizer | HIV infection AIDs, (CCR5 antagonist, in development) |
| Trizivir ® | GSK | HIV infection AIDs, (three drug combination) |
| PA-457 | Panacos | HIV infection AIDs, (maturation Inhibitor, in development) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| BMS-707035 | Bristol-Myers Squibb | HIV infection AIDs, (viral integrase Inhibitor) |
| Integrase Inhibitor MK-0518 | Merck | HIV infection AIDs, viral integrase inhibitor in development |
| Truvada ® | Gilead | Combination of Tenofovir disoproxil fumarate salt (Viread ®) and Emtriva ® (Emtricitabine) |
| Integrase Inhibitor GS917/JTK-303 | Gilead/Japan Tobacco | HIV Infection AIDs, viral integrase inhibitor in development |
| Triple drug combination | Gilead/ Bristol-Myers Squibb | Combination of Tenofovir disoproxil fumarate salt (Viread ®), Emtriva ® (Emtricitabine), and Sustiva ® (Efavirenz) |

-continued

| Drug Name | Manufacturer | Indication |
|---|---|---|
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine- Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |

-continued

| Drug Name | Manufacturer | Indication |
|---|---|---|
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulene | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein may be used in combination with another class of agents for treating AIDS which are called HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells.* Meanwell, Nicholas A.; Kadow, John F. Current Opinion in Drug Discovery & Development (2003), 6(4), 451-461. Specifically the compounds can be utilized in combination with other attachment inhibitors, fusion inhibitors, and chemokine receptor antagonists aimed at either the CCR5 or CXCR4 coreceptor.

It will be understood that the scope of combinations of the compounds of this disclosure with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is Reyataz® (active ingredient Atazanavir). Typically a dose of 300 to 600 mg is administered once a day. This may be co-administered with a low dose of Ritonavir (50 to 500 mgs). Another preferred inhibitor of HIV protease is Kaletra®. Another useful inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present disclosure and other active agents may be administered separately or in conjunction. In addition, the administration of one element may be prior to, concurrent to, or subsequent to the administration of other agent(s).

Preferred combinations are simultaneous or alternating treatments of with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present disclosure and other active agents may be administered separately or in conjunction. In addition, the administration of one element may be prior to, concurrent to, or subsequent to the administration of other agent(s).

Abbreviations

The following abbreviations, most of which are conventional abbreviations well known to those skilled in the art, are used throughout the description of the disclosure and the examples. Some of the abbreviations used are as follows:

| | |
|---|---|
| h = | hour(s) |
| rt = | room temperature |
| mol = | mole(s) |
| mmol = | millimole(s) |
| g = | gram(s) |
| mg = | milligram(s) |
| mL = | milliliter(s) |
| TFA = | trifluoroacetic Acid |
| DCE = | 1,2-Dichloroethane |
| $CH_2Cl_2$ = | dichloromethane |
| TPAP = | tetrapropylammonium perruthenate |
| THF = | tetrahydofuran |
| DEPBT = | 3-(diethoxyphosphoryloxy)-1,2,3-benzotriazin-4(3H)-one |
| DMAP = | 4-dimethylaminopyridine |

-continued

| | |
|---|---|
| P-EDC = | polymer supported 1-(3-dimethylaminopropyl)-3-ethylcarbodiimide |
| EDC = | 1-(3-dimethylaminopropyl)-3-ethylcarbodiimide |
| DMF = | N,N-dimethylformamide |
| Hunig's Base = | N,N-diisopropylethylamine |
| MCPBA = | meta-chloroperbenzoic Acid |
| azaindole = | 1H-pyrrolo-pyridine |
| 4-azaindole = | 1H-pyrrolo[3,2-b]pyridine |
| 5-azaindole = | 1H-pyrrolo[3,2-c]pyridine |
| 6-azaindole = | 1H-pyrrolo[2,3-c]pyridine |
| 7-azaindole = | 1H-pyrrolo[2,3-b]pyridine |
| PMB = | 4-methoxybenzyl |
| DDQ = | 2,3-dichloro-5,6-dicyano-1,4-benzoquinone |
| OTf = | trifluoromethanesulfonoxy |
| NMM = | 4-methylmorpholine |
| PIP-COPh = | 1-benzoylpiperazine |
| NaHMDS = | sodium hexamethyldisilazide |
| EDAC = | 1-(3-dimethylaminopropyl)-3-ethylcarbodiimide |
| TMS = | trimethylsilyl |
| DCM = | dichloromethane |
| DCE = | dichloroethane |
| MeOH = | methanol |
| THF = | tetrahydrofuran |
| EtOAc = | ethyl acetate |
| LDA = | lithium diisopropylamide |
| TMP-Li = | 2,2,6,6-tetramethylpiperidinyl lithium |
| DME = | dimethoxyethane |
| DIBALH = | diisobutylaluminum hydride |
| HOBT = | 1-hydroxybenzotriazole |
| CBZ = | benzyloxycarbonyl |
| PCC = | pyridinium chlorochromate |

The compounds of the present disclosure may be administered orally, parenterally (including subcutaneous injections, intravenous, intramuscular, intrasternal injection or infusion techniques), by inhalation spray, or rectally, in dosage unit formulations containing conventional non-toxic pharmaceutically acceptable carriers, adjuvants and diluents.

Thus, in accordance with the present disclosure, there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically effective amount of a compound of the present disclosure.

The pharmaceutical composition may be in the form of orally administrable suspensions or tablets; nasal sprays, sterile injectable preparations, for example, as sterile injectable aqueous or oleagenous suspensions or suppositories.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this disclosure can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Chemistry

The present disclosure comprises compounds of Formula I, their pharmaceutical formulations, and their use in patients suffering from or susceptible to HIV infection. The compounds of Formula I include pharmaceutically acceptable salts thereof. General procedures to construct compounds of Formula I and intermediates useful for their synthesis are described in the following Schemes.

Chemistry Schemes:

The compounds of the present disclosure can be made by a variety of ways. Non-limiting examples of these schemes include Schemes 1-6 below.

SCHEME 1

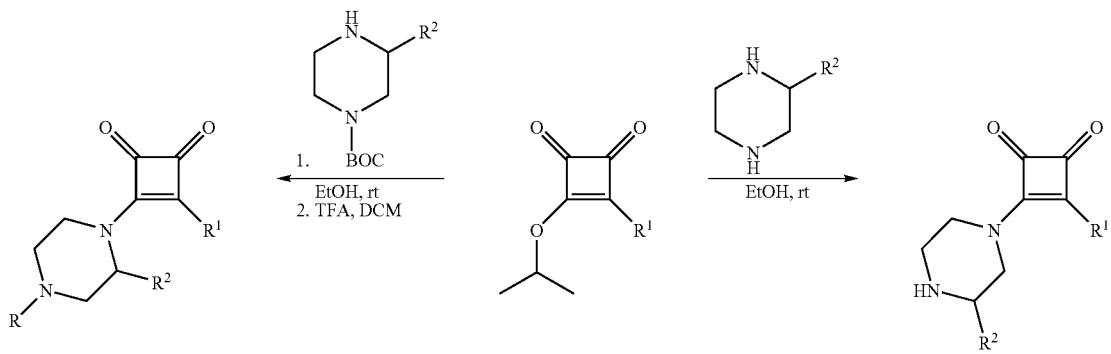

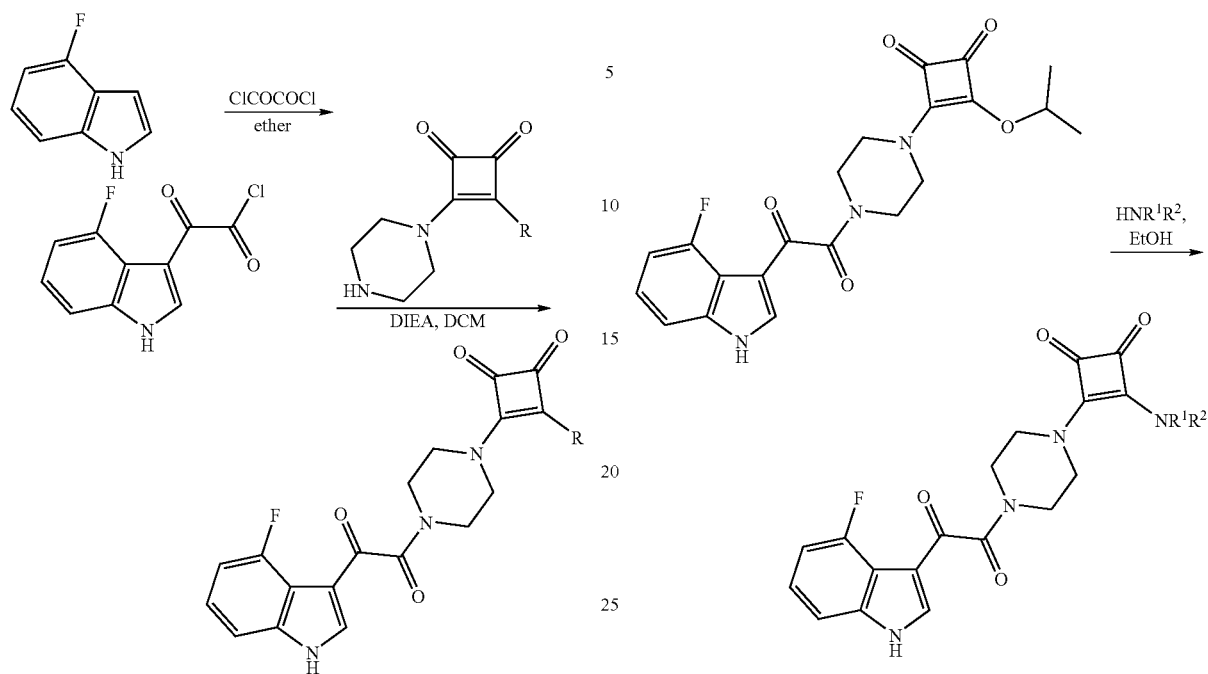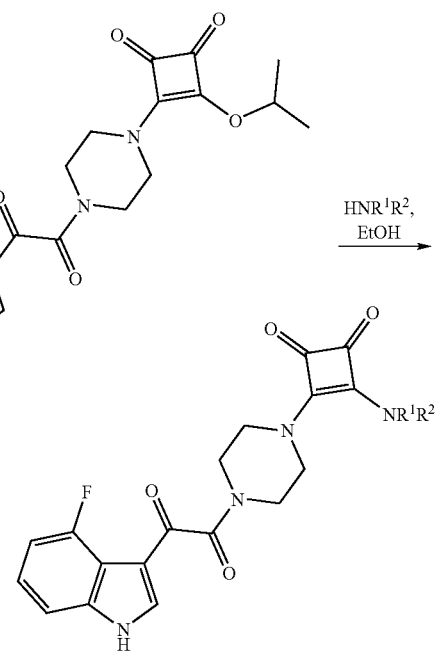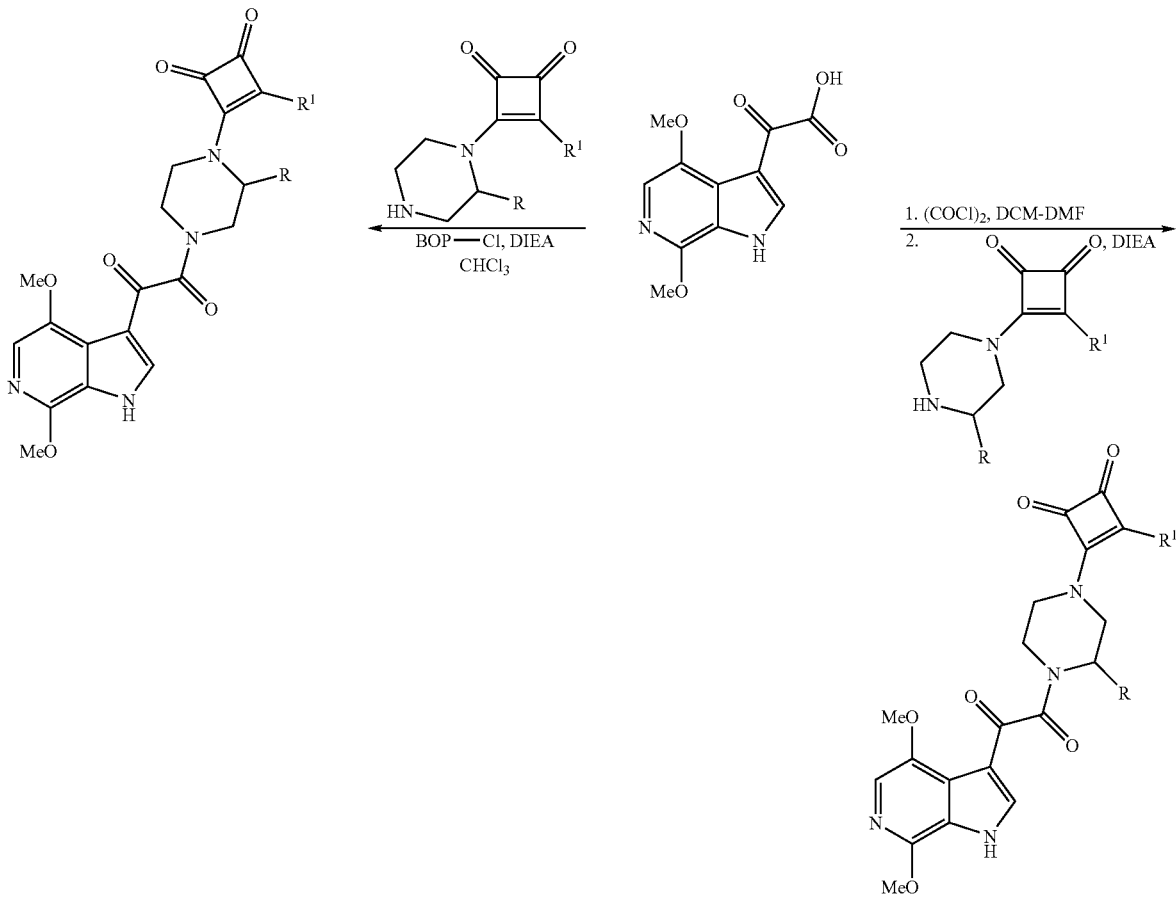

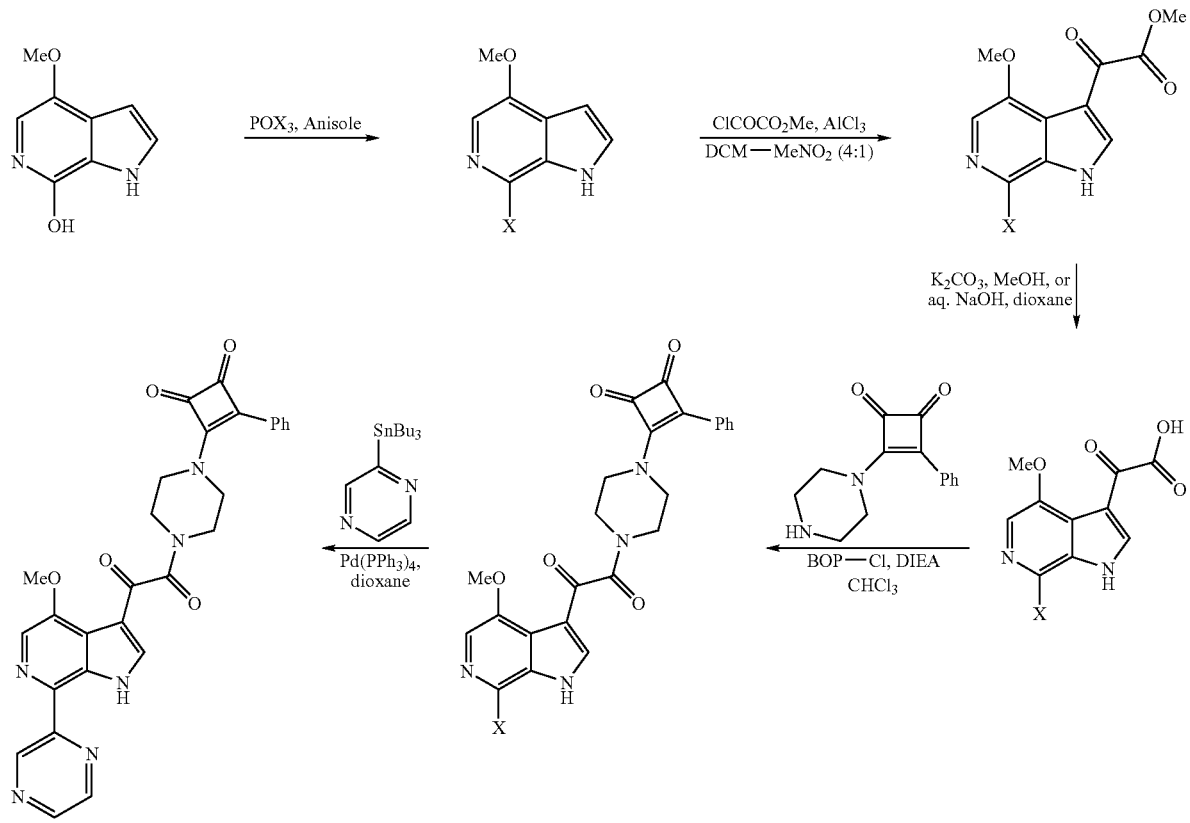
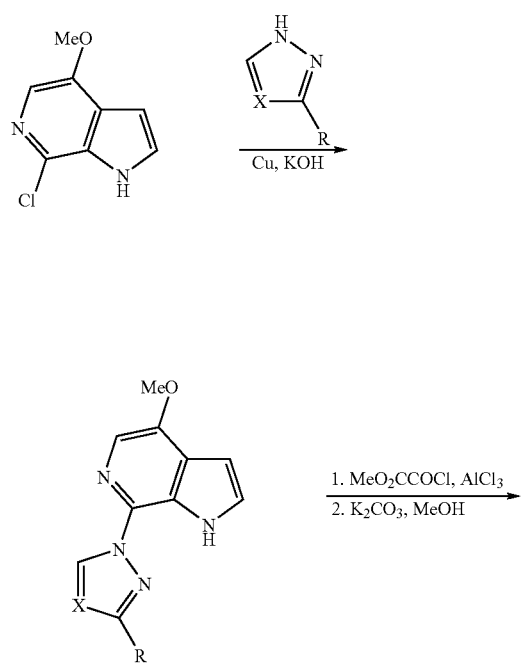
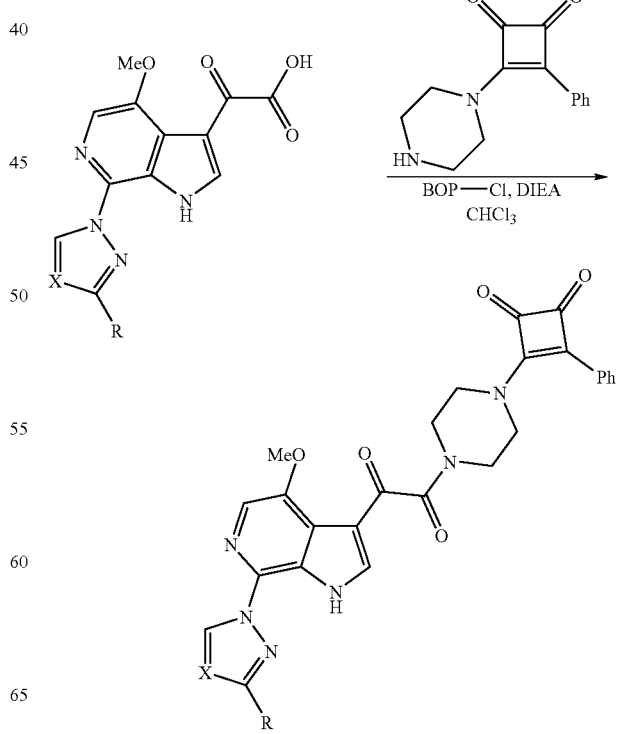

EXAMPLES

The following examples illustrate typical syntheses of the compounds of Formula I as described generally above. These examples are illustrative only and are not intended to limit the disclosure in any way. The reagents and starting materials are readily available to one of ordinary skill in the art.

Chemistry

General Experimental:
FT-IR: Spectra were acquired using a Nicolet Protégé 460 spectrometer, with samples prepared as either thin films or KBr pellets.
$^1$HNMR: Spectra were acquired on a Bruker Avance 400 spectrometer in the designated solvents. Chemical shifts are reported in ppm (δ) using the deuterated solvent as internal standard.
LCMS: Analyses were done using a Shimadzu LC-10AT/ Micromass ZMD or ZQ system, in negative and/or positive ion mode, under the following conditions:
Start % B=0
Final % B=100
Gradient time=2 min
Hold time=1 min
Flow Rate=4 mL/min
Wavelength=220 nm
Solvent A=10% MeCN— 90% $H_2O$— 5 mM $NH_4OAc$ (or 0.05% TFA)
Solvent B=90% MeCN— 10% $H_2O$— 5 mM $NH_4OAc$ (or 0.05% TFA)
Column=Primesphere C18-HC 4.6×30 mm (unless otherwise specified)
Prep HPLC: Separations were done using a Shimadzu LC-8A system under the following conditions:
Start % B=20
Final % B=100
Gradient time=8 min
Hold time=4 min
Flow Rate=30 mL/min
Wavelength=220 nm
Solvent A=10% MeCN— 90% $H_2O$— 5 mM $NH_4OAc$ (or 0.1% TFA)
Solvent B=90% MeCN— 10% $H_2O$— 5 mM $NH_4OAc$ (or 0.1% TFA)
Column=YMC Pack C-18 30×100 mm (unless otherwise specified)

Example 1

As illustrated in Scheme 1, 3-isopropoxy-4-substituted-cyclobut-3-ene-1,2-diones were conveniently used as precursors, being prepared from either 3,4-diisopropoxy-cyclobut-3-ene-1,2-dione (cf L. S. Liebeskind, et al., *J. Org. Chem.* 1988, 53, 2482) or from 3-isopropoxy-4-(tri-n-butylstannyl)-cyclobut-3-ene-1,2-dione (cf L. S. Liebeskind, et al., *J. Org. Chem.* 1993, 58, 3543) according to methods well-documented in the literature. Subsequent reaction of these precursors with piperazine or a 2-substituted-piperazine in a suitable solvent, as for example ethanol, afforded the intermediate 3-piperazinyl-4-substituted-cyclobut-3-ene-1, 2-diones. Alternatively, this reaction could be done in analogous fashion using a suitably protected piperazine or 3-substituted-piperazine (using for example a BOC or similar amine protecting group well-known to one skilled in the art), with the proviso that the protecting group be removed before proceeding to the next step. In the case of a BOC group, this was conveniently done using an acid, as for example TFA, in a suitable solvent such as dichloromethane.

Following compounds A1-A15 were prepared:

A1:

3-(1-Piperazinyl)-4-(2-thienyl)-cyclobut-2-ene-1,2-dione

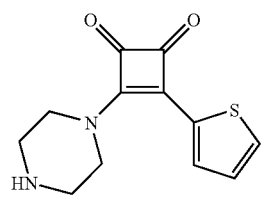

A solution of 3-isopropoxy-4-(2-thienyl)-cyclobut-3-ene-1,2-dione (0.500 g, 2.25 mmol; prepared according to the procedure of L. S. Liebeskind, et al., *J. Org. Chem.* 1988, 53, 2482) in EtOH (10 mL) was cooled at 5° C. under Ar and piperazine (0.194 g, 2.25 mmol) was added all at once. The reaction mixture was stirred at room temperature for 2 h and then it was filtered and the filtercake washed with EtOH (3×4 mL). The resulting filtrate was then evaporated to afforded the title compound (0.120 g, 22%) as a colorless oil which solidified on standing at room temperature.

IR (KBr) 1597 cm$^{-1}$; $^1$HNMR (400 MHz, CDCl$_3$) δ 7.71 (d, J=3.6 Hz, 1H), 7.53 (d, J=5.0 Hz, 1H), 7.14 (t, J=4.0 Hz, 1H), 4.06 (m, 2H), 3.81 (m, 2H), 2.99 (m, 4H). LCMS m/e 249 (M+H)$^+$.

A2:

3-(1-Piperazinyl)-4-(2-furyl)-cyclobut-2-ene-1,2-dione

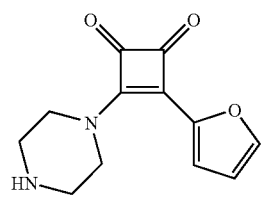

Prepared using a general method as exemplified by the preparation of Compound A1; title compound is a colorless oil which solidified on standing at room temperature (34% yield);

IR (KBr) 1615 cm$^{-1}$; $^1$HNMR (400 MHz, CDCl$_3$) δ 7.55 (d, J=2.0 Hz, 1H), 7.43 (d, J=3.5 Hz, 1H), 6.57 (d, J=3.5 Hz, 1H), 4.07 (t, J=5.1 Hz, 2H), 3.98 (t, J=5.1 Hz, 2H), 3.02 (t, J=5.1 Hz, 2H), 2.96 (t, J=5.1 Hz, 2H); LCMS m/e 233 (M+H)$^+$.

A3:

3-(1-Piperazinyl)-4-(2-thiazolyl)-cyclobut-2-ene-1,2-dione

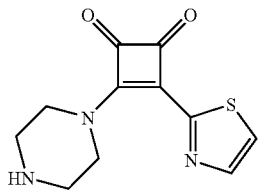

Prepared using a general method as exemplified by the preparation of Compound A1; the title compound is a yellow oil (94% yield);

IR (film) 1599 cm$^{-1}$; $^1$HNMR (400 MHz, CDCl$_3$) δ 7.98 (m, 1H), 7.70 (d, J=3.0 Hz, 1H), 7.31 (d, J=3.5 Hz, 1H), 4.78 (m, 1H), 3.59 (m, 2H), 3.25 (m, 1H), 3.05 (m, 1H), 2.90 (m, 1H), 2.80 (m, 2H), 2.60 (m, 1H); LCMS m/e 250 (M+H)$^+$.

A4:

3-(1-Piperazinyl)-4-(2-oxazolyl)-cyclobut-2-ene-1,2-dione

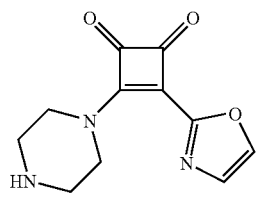

Prepared using a general method as exemplified by the preparation of Compound A1; the title compound is a brown solid (74% yield);

IR (film) 1629 cm$^{-1}$; $^1$HNMR (400 MHz, CDCl$_3$) δ 8.62 (s, 1H), 7.90 (s, 1H), 4.3 (t, J=5.0 Hz, 2H), 4.06 (t, J=5.0 Hz, 2H), 3.01 (t, J=5.0 Hz, 2H), 2.97 (t, J=5.5 Hz, 2H). LCMS m/e 234 (M+H)$^+$.

A5:

3-(1-Piperazinyl)-4-phenyl-cyclobut-2-ene-1,2-dione

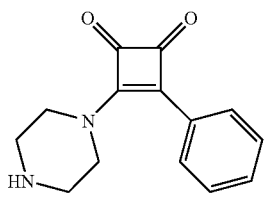

Prepared using a general method as exemplified by the preparation of Compound A1; the title compound is a yellow oil (68% yield);

IR (film) 1609 cm$^{-1}$; $^1$HNMR (400 MHz, CDCl$_3$) δ 7.48 (d, J=7.1 Hz, 2H), 7.41 (m, 2H), 7.35 (m, 1H), 4.04 (m, 2H), 3.52 (m, 2H), 2.97 (m, 2H), 2.91 (m. 2H). LCMS m/e 243 (M+H)$^+$.

A6:

3-[3-(R)-Methylpiperazin-1-yl]-4-phenyl-cyclobut-2-ene-1,2-dione

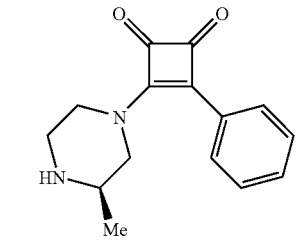

Prepared using a general method as exemplified by the preparation of Compound A1; the title compound as a yellow foam material (quantitative yield);

IR (film) 1607 cm$^{-1}$; $^1$HNMR (400 MHz, CDCl$_3$) δ 11.52 (m, 1H), 7.47 (m, 2H), 7.38 (m, 3H), 4.74 (m, 1H), 3.71 (m, 1H), 3.31 (m, 1H), 3.08 (m, 1H), 2.93 (m, 4H), 1.07 (m, 3H). LCMS m/e 257 (M+H)$^+$.

A7:

3-[3-(S)-Methylpiperazin-1-yl]-4-phenyl-cyclobut-2-ene-1,2-dione

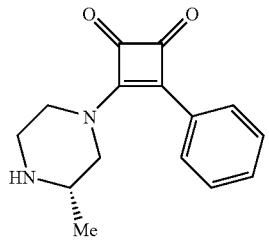

Prepared using a general method as exemplified by the preparation of Compound A1; the title compound is a yellow foam material (quantitative yield);

IR (film) 1607 cm$^{-1}$. $^1$HNMR (400 MHz, CDCl$_3$) δ 11.50 (m, 1H), 7.47 (m, 2H), 7.39 (m, 3H), 4.74 (m, 1H), 3.71 (m, 1H), 3.32 (m, 1H), 3.09 (m, 1H), 2.94 (m, 4H), 1.07 (m, 3H). LCMS m/e 257 (M+H)$^+$.

A8:

3-(1-Piperazinyl)-4-butyl-cyclobut-2-ene-1,2-dione

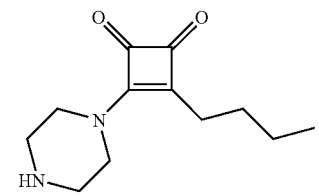

Prepared using a general method as exemplified by the preparation of Compound A1; the title compound is an oil (95% yield);

IR (KBr) 1599 cm⁻¹. ¹HNMR (400 MHz, CDCl₃) δ 3.91 (t, J=5.1 Hz, 2H), 3.46 (t, J=5.1 Hz, 2H), 2.95 (t, J=5.1 Hz, 2H), 2.91 (t, J=5.1 Hz, 2H), 2.57 (t, J=7.6 Hz, 2H), 1.57 (m, 2H), 1.33 (m, 2H), 0.88 (t, J=7.6 Hz, 3H). LCMS m/e 223 (M+H)⁺.

A9:

3-(1-Piperazinyl)-4-tert-butyl-cyclobut-2-ene-1,2-dione

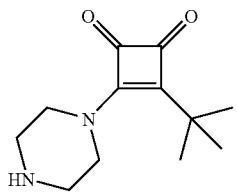

Prepared using a general method as exemplified by the preparation of Compound A1; the title compound is a solid (94% yield);

IR (KBr) 1585 cm⁻¹. ¹HNMR (400 MHz, CDCl₃) δ 3.83 (m, 4H), 2.93 (t, J=5.1 Hz, 4H), 1.33 (s, 9H). LCMS m/e 223 (M+H)⁺.

A10:

3-(1-Piperazinyl)-4-benzyl-cyclobut-2-ene-1,2-dione

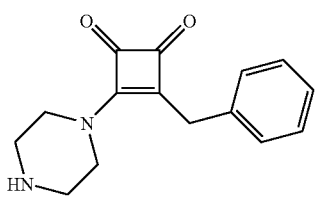

Prepared using a general method as exemplified by the preparation of Compound A1; the title compound is an oil (98% yield);

IR (KBr) 1602 cm⁻¹; ¹HNMR (400 MHz, CDCl₃) δ 7.25 (m, 2H), 7.19 (m, 1H), 7.11 (m, 2H), 3.94 (s, 2H), 3.87 (t, J=5.1 Hz, 2H), 3.24 (t, J=5.1 Hz, 2H), 2.83 (t, J=5.1 Hz, 2H), 2.58 (t, J=5.1 Hz, 2H). LCMS m/e 257 (M+H)⁺.

A11:

3-(1-Piperazinyl)-4-isopropoxy-cyclobut-2-ene-1,2-dione

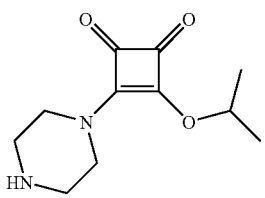

Prepared using a general method as exemplified by the preparation of Compound A1; the title compound is an oil which solidified on standing at room temperature (71% yield);

IR (KBr) 1611 cm⁻¹. ¹HNMR (400 MHz, CDCl₃) δ 5.36 (m, 1H), 3.82 (m, 2H), 3.52 (m, 2H), 2.90 (m, 4H), 1.36 (d, J=6.1 Hz, 6H). LCMS m/e 225 (M+H)⁺.

A12:

3-[2-(S)-Methylpiperazin-1-yl]-4-phenyl-cyclobut-2-ene-1,2-dione

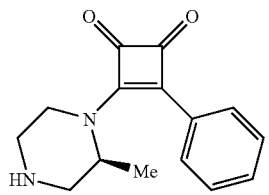

To an ice-cold suspension of 3-(S)-methyl-1-(tert-butoxycarbonyl)piperazine (0.200 g, 1.00 mmol) in ethanol (4 mL) was added 3-isopropoxy-4-phenylcyclobut-3-ene-1,2-dione (0.216 g, 1.00 mmol) and the mixture was then stirred at room temperature under Ar for 5 days. The volatiles were then removed in vacuo and the residue was taken up in dichloromethane (5 mL). The solution was cooled at 5° C. and then TFA (2 mL) was added and stirring was continued at room temperature for 16 h. The volatiles were then removed in vacuo and the residue partitioned with EtOAc-1M NaHCO₃. The organic phase was separated, washed (brine), dried (MgSO₄) and evaporated to give the essentially pure title compound (0.196 g, 77%) as a yellow solid.

IR (film) 1591 cm⁻¹. ¹HNMR (400 MHz, THF-d₈) δ 10.80 (m, 1H), 7.54 (d, J=7.1 Hz, 2H), 7.44 (t, J=7.1 Hz, 2H), 7.36 (t, J=7.1 Hz, 2H), 3.01 (m, 2H), 2.86 (m, 3H), 2.74 (m, 2H), 1.50 (d, J=6.6 Hz, 3H). LCMS m/e 257 (M+H)⁺.

A13:

3-[2-(R)-Methylpiperazin-1-yl]-4-phenyl-cyclobut-2-ene-1,2-dione

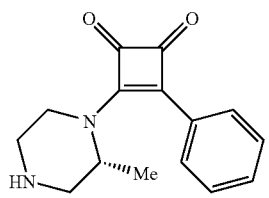

Prepared using a general method as exemplified by the preparation of Compound A12;

the title compound as a yellow solid (80% yield);

title compound is a yellow solid;

IR (film) 1590 cm⁻¹. ¹HNMR (400 MHz, THF-d₈) δ 10.85 (m, 1H), 7.56 (d, J=7.1 Hz, 2H), 7.43 (t, J=7.6 Hz, 2H), 7.35 (d, J=7.1 Hz, 1H), 2.99 (m, 2H), 2.82 (m, 3H), 2.70 (m, 2H), 1.47 (d, J=6.6 Hz, 3H). LCMS m/e 257 (M+H)⁺.

A14:

3-(4-tert-butoxycarbonylpiperazin-1-yl)-4-(4-fluorophenyl)-cyclobut-2-ene-1,2-dione

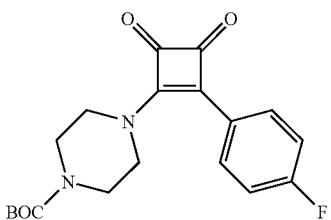

Prepared using a general method as exemplified by the preparation of Compound A12;

Starting materials: 1-tert-butoxycarbonylpiperazine and 3-isopropoxy-4-(4-fluorophenyl)-cyclobut-3-ene-1,2-dione (in turn prepared according to the procedure of L. S. Liebeskind, et al., *J. Org. Chem.* 1993, 58, 3543), without the use of TFA to remove the N-BOC protecting group.

the title compound is a white solid (quantitative yield);

IR (film) 1611 cm$^{-1}$. $^1$HNMR (400 MHz, CDCl$_3$) δ 7.55-7.45 (m, 2H), 7.11 (t, J=8.6 Hz, 2H), 4.00 (m, 2H), 3.50 (m, 6H), 1.41 (s, 9H).

A15:

3-(4-tert-butoxycarbonylpiperazin-1-yl)-4-(4-methoxyphen-yl)-cyclobut-2-ene-1,2-dione

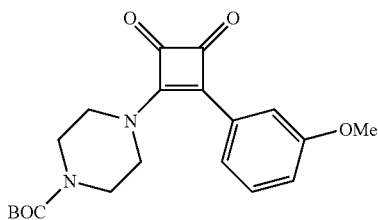

Prepared using a general method as exemplified by the preparation of Compound A12;

Starting material: 1-tert-butoxycarbonylpiperazine and 3-isopropoxy-4-(3-methoxyphenyl)-cyclobut-3-ene-1,2-dione (in turn prepared according to the procedure of L. S. Liebeskind, et al., *J. Org. Chem.* 1993, 58, 3543), without the use of TFA to remove the N—BOC protecting group.

The title compound as a white solid (quantitative yield);

IR (film) 1612 cm$^{-1}$. $^1$HNMR (400 MHz, CDCl$_3$) δ 7.31 (t, J=8.1 Hz, 1H), 7.03 (m, 1H), 6.99 (m, 1H), 6.90 (m, 1H), 4.01 (m, 2H), 3.78 (s, 3H), 3.52 (m, 6H), 1.40 (s, 9H).

Example 2

As illustrated in Scheme 2, a series of indole-3-(2-oxo) acetic acid derivatives were conveniently prepared by reacting an indole, as for example 4-fluoroindole, with oxalyl chloride in ether. The resulting acid chloride derivative was readily reacted with any of a series of 3-piperazinyl-4-substituted-cyclobut-3-ene-1,2-diones in the presence of a suitable amine base in an appropriate solvent, as for example diisopropylethylamine in dichloromethane, to afford the corresponding desired amide derivatives.

The compounds B1-B8 were prepared.

B1:

2-(4-Fluoro-1H-indol-3-yl)-2-oxoacetyl chloride

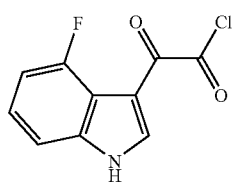

To a stirred solution of 4-fluoroindole (2.00 g, 14.8 mmol) in ether (15 mL), at 0° C. under Ar, was added oxalyl chloride (1.55 mL, 17.8 mmol) dropwise. The resulting suspension was stirred at room temperature for 1 h and then it was filtered and the filtercake was washed with ether. The resulting solid was dried in vacuo to give the title compound (2.60 g, 78%) as a yellow powder:

$^1$HNMR (400 MHz, DMSO-d$_6$) δ 12.62 (s, 1H), 8.37 (d, J=3.5 Hz, 1H), 7.36 (m, 1H), 7.26 (m, 1H), 6.99 (dd, J=7.8, 10.9 Hz, 1H). LCMS m/e 226 (M+H)$^+$.

B2:

3-[4-[2-(4-Fluoro-1H-indol-3-yl)-2-oxoacetyl]piperazin1-yl]-4-(2-thienyl)-cyclobut-3-ene-1,2-dione

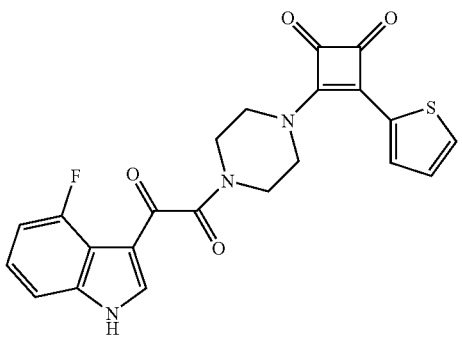

To a suspension of 2-(4-fluoro-1H-indol-3-yl)-2-oxoacetyl chloride (g, 0.27 mmol) in dichloromethane (4 mL), cooled at 5° C. under Ar, was added 3-(1-piperazinyl)-4-(2-thienyl)-cyclobut-2-ene-1,2-dione (g, 0.27 mmol) and then DIEA (mL, 0.30 mmol). The mixture was stirred at the same temperature for 1 h and then it was diluted with EtOAc (20 mL), washed (sat. NaHCO$_3$, brine), dried (MgSO$_4$) and evaporated. The residue was purified by preparative HPLC (C-18/10-90% MeCN-5 mmolar aqueous NH$_4$OAc) to give the title compound (0.062 g, 53%) as a yellow solid:

IR (KBr) 1600 cm$^{-1}$. $^1$HNMR (400 MHz, DMSO-d$_6$) δ 8.31 (s, 1H), 7.94 (m, 1H), 7.62 (m, 1H), 7.29 (m, 3H), 7.01 (t, J=8.1 Hz, 1H), 4.15 (m, 1H), 3.97 (m, 2H), 3.85 (m, 2H), 3.79 (m, 1H), 3.61 (m, 2H). LCMS m/e 436 (M–H)$^-$.

B3:

3-[4-[2-(4-Fluoro-1H-indol-3-yl)-2-oxoacetyl]piperazin1-yl]-4-(2-furyl)-cyclobut-3-ene-1,2-dione

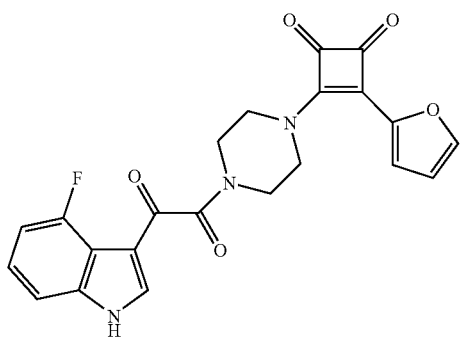

Prepared using a general method as exemplified by the preparation of Compound B2; the title compound is a yellow solid (48% yield):

IR (KBr) 1613 cm$^{-1}$. $^1$HNMR (400 MHz, DMSO-d$_6$) δ 8.30 (d, J=6.1 Hz, 1H), 8.08 (s, 0.5H), 7.88 (s, 0.5H), 7.30 (m, 3H), 7.00 (t, J=8.6 Hz, 1H), 6.80 (d, J=5.1 Hz, 0.5H), 6.73 (d, J=5.1 Hz, 0.5H), 4.14 (m, 2H), 3.97 (m, 2H), 3.84 (m, 2H), 3.59 (m, 2H). LCMS m/e 420 (M−H)$^-$.

B4:

3-[4-[2-(4-Fluoro-1H-indol-3-yl)-2-oxoacetyl]piperazin1-yl]-4-phenyl-cyclobut-3-ene-1,2-dione

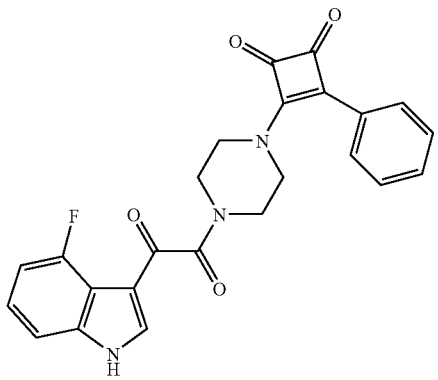

Prepared using a general method as exemplified by the preparation of Compound B2; the title compound as a white solid (21% yield):

IR (film) 1552 cm$^{-1}$. $^1$HNMR (400 MHz, THF-d$_8$) δ 11.52 (m, 1H), 8.10 (Br s, 1H), 7.61 (m, 2H), 7.41 (m, 3H), 7.21 (m, 2H), 6.89 (t, J=8.1 Hz, 1H), 4.15 (m, 2H), 3.76 (m, 6H). LCMS m/e 430 (M−H)$^-$.

B5:

3-[4-[2-(4-Fluoro-1H-indol-3-yl)-2-oxoacetyl]piperazin1-yl]-4-butyl-cyclobut-3-ene-1,2-dione

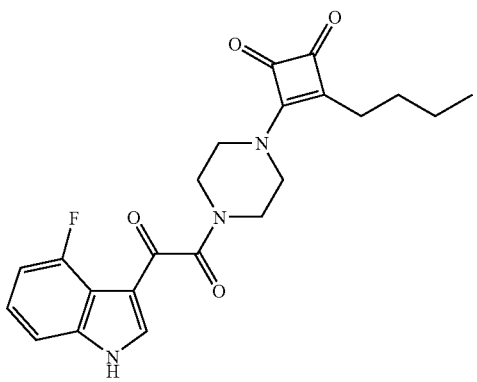

Prepared using a general method as exemplified by the preparation of Compound B2; the title compound is a yellow solid (55% yield):

IR (film) 1598 cm$^{-1}$. $^1$HNMR (400 MHz, CDCl$_3$) δ 9.34 (m, 1H), 7.99 (br s, 1H), 7.18 (m,1H), 6.92 (m, 1H), 4.08 (m, 1H), 4.01 (m, 1H), 3.90-3.80 (m, 2H), 3.70-3.55 (m, 4H), 2.63 (t, J=7.6 Hz, 1H), 2.55 (t, J=7.6 Hz, 1H), 1.58(m, 2H), 1.33 (m,2H), 0.91 (t, J=7.6 Hz, 1.5H), 0.85 (t, J=7.6 Hz, 1.5H). LCMS m/e 412 (M+H)$^+$.

B6:

3-[4-[2-(4-Fluoro-1H-indol-3-yl)-2-oxoacetyl]piperazin1-yl]-4-tert-butyl-cyclobut-3-ene-1,2-dione

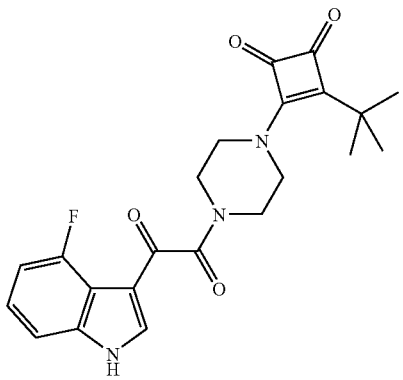

Prepared using a general method as exemplified by the preparation of Compound B2; the title compound is a white solid (61% yield):

IR (film) 1582 cm$^{-1}$. $^1$HNMR (400 MHz, CDCl$_3$) δ 9.48 (br s, 1H), 7.97 (d, J=3.5 Hz, 1H), 7.17 (m, 2H), 6.91 (m, 1H), 3.96 (m, 4H), 3.85 (m, 2H), 3.64 (m, 2H), 1.34 (s, 9H). LCMS m/e 410 (M−H)$^-$.

B7:

3-[4-[2-(4-Fluoro-1H-indol-3-yl)-2-oxoacetyl]piperazin1-yl]-4-benzyl-cyclobut-3-ene-1,2-dione

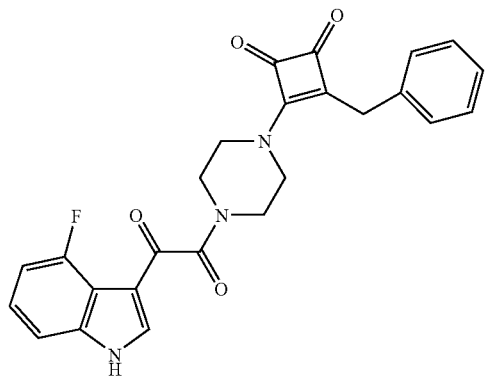

Prepared using a general method as exemplified by the preparation of Compound B2; the title compound is a beige solid (38% yield):

IR (KBr) 1595 cm$^{-1}$. $^1$HNMR (400 MHz, CDCl$_3$) δ 9.08 (m, 1H), 7.95 (br s, 1H), 7.30 (t, J=7.6 Hz, 1H), 7.21 (m, 4H), 7.14 (d, J=7.1 Hz, 1H), 7.06 (d, J=7.1 Hz, 1H), 6.92 (m, 1H), 4.04 (t, J=5.1 Hz, 1H), 3.99 (s, 1H), 3.96 (t, J=5.1 Hz, 1H), 3.92 (s, 1H), 3.75 (t, J=5.1 Hz, 1H), 3.52 (t, J=5.1 Hz, 1H), 3.36 (m, 3H), 3.21 (t, J=5.1 Hz, 1H). LCMS m/e 446 (M+H)$^+$.

B8:

3-[4-[2-(4-Fluoro-1H-indol-3-yl)-2-oxoacetyl]piperazin1-yl]-4-isopropoxy-cyclobut-3-ene-1,2-dione

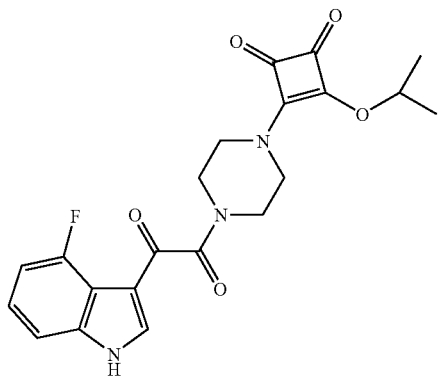

To a solution of 3-(1-piperazinyl)-4-isopropoxy-cyclobut-2-ene-1,2-dione (0.400 g, 1.79 mmol) in dichloromethane (10 mL), cooled at 5° C. under Ar, was added DIEA (0.35 mL, 2.00 mmol), followed by a solution of 2-(4-fluoro-1H-indol-3-yl)-2-oxoacetyl chloride (0.403 g, 1.79 mmol) in dichloromethane (10 mL). The mixture was stirred at the same temperature for 1 h and then it was evaporated.

The residue was purified by flash chromatography (SiO$_2$/hexane-EtOAc, 4:1 to 0:1 then DCM-MeCN, 1:1) to give the title compound (0.612 g, 83%) as a white solid:

IR (film) 1598 cm$^{-1}$. $^1$HNMR (400 MHz, THF-d$_8$) δ 11.51 (m, 1H), 8.10 (br s, 1H), 7.21 (m, 2H), 6.90 (t, J=8.1 Hz, 1H), 5.35 (m, 1H), 3.93 (m, 4H), 3.80 (m, 2H), 3.70 (m, 2H), 1.40 (d, J=6.6 Hz, 6H). LCMS m/e 412 (M−H)$^-$.

Example 3

As series of aminocyclobut-3-ene-1,2-dione derivatives were prepared as exemplified in Scheme 3. Thus, reaction of a 3-isopropoxy-4-(piperazin-1-yl)-cyclobut-3-ene-1,2-dione derivative with a primary or secondary amine in an appropriate solvent, as for example ethanol at room temperature to 80° C., afforded the corresponding 3-amino-4-(piperazin-1-yl)-cyclobut-3-ene-1,2-dione derivatives.

3-[4-[2-(4-Fluoro-1H-indol-3-yl)-2-oxoacetyl]piperazin1-yl]-4-dimethylamino-cyclobut-3-ene-1,2-dione

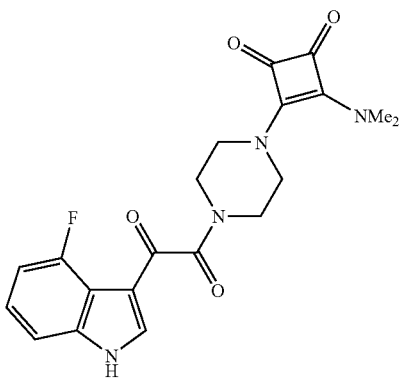

To a saturated solution of dimethylamine in ethanol (2 mL), cooled at 5° C. under Ar, was added 3-[4-[2-(4-fluoro-1H-indol-3-yl)-2-oxoacetyl]piperazin1-yl]-4-isopropoxy-cyclobut-3-ene-1,2-dione (0.020 g, 0.048 mmol) and the mixture was then allowed to stir at room temperature for 2 h. The volatiles were then removed in vacuo to give the essentially pure title compound (0.019 g, 99%) as a white solid:

IR (KBr) 1586 cm$^{-1}$. $^1$HNMR (400 MHz, THF-d$_8$) δ 11.50 (br s, 1H), 8.08 (s, 1H), 7.23 (d, J=8.1 Hz, 1H), 7.24-7.16 (m, 1H), 6.88 (dd, J=7.6, 10.2 Hz, 1H), 3.79 (d, J=6.1 Hz, 2H), 3.73 (d, J=6.1 Hz, 2H), 3.58 (m, 4H), 3.19 (s, 6H). LCMS m/e 397 (M−H)$^-$.

A series of related compounds were prepared in analogous fashion, with the following modifications; a solution of 3-[4-[2-(4-fluoro-1H-indol-3-yl)-2-oxoacetyl]piperazin1-yl]-4-isopropoxy-cyclobut-3-ene-1,2-dione (0.043 mmol) in ethanol (1.5 mL) was treated with the desired amine (0.129 mmol) and the reaction mixture was heated at 80° C. for 2-3 h. The volatiles were then removed in vacuo and the residue was taken up in DMF and purified by preparative HPLC (C-18/10-90% MeCN-5 mmolar aqueous NH$_4$OAc) to give the corresponding product (see Table 1).

TABLE 1

Representative aminocyclobut-3-ene-1,2-dione derivatives

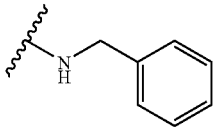

| Example | —NR¹R² | LCMS m/e (M − H)⁻ |
|---|---|---|
| 1 | 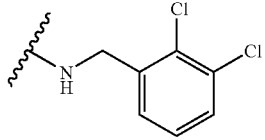 N-benzyl | 459 |
| 2 | 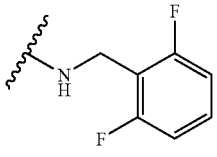 2,3-dichlorobenzyl | 527 |
| 3 | 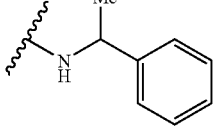 2,6-difluorobenzyl | 495 |
| 4 | 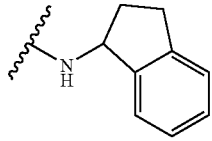 α-methylbenzyl | 473 |
| 5 | 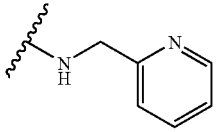 indanyl | 485 |
| 6 | 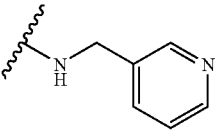 2-pyridylmethyl | 460 |
| 7 | 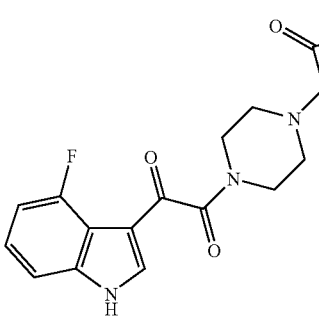 3-pyridylmethyl | 460 |

TABLE 1-continued

Representative aminocyclobut-3-ene-1,2-dione derivatives

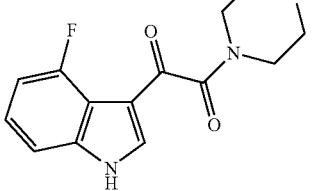

| Example | —NR¹R² | LCMS m/e (M − H)⁻ |
|---|---|---|
| 8 | 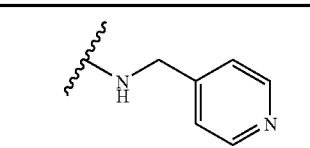 4-pyridylmethyl | 460 |
| 9 | 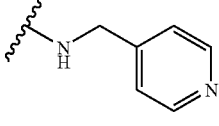 2-thienylmethyl | 465 |
| 10 | 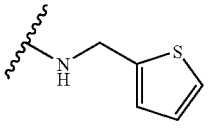 2-furylmethyl | 449 |
| 11 | 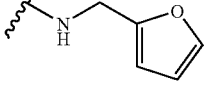 phenethyl | 473 |
| 12 | 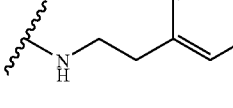 2-(pyrrolidin-1-yl)ethyl | 466 |
| 13 | 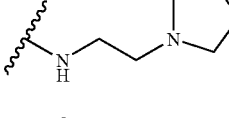 (tetrahydrofuran-2-yl)methyl | 453 |
| 14 | 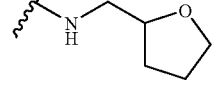 cyclohexyl | 451 |
| 15 | 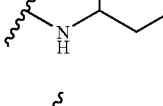 thiomorpholinyl | 455 |

TABLE 1-continued

Representative aminocyclobut-3-ene-1,2-dione derivatives

| Example | —NR$^1$R$^2$ | LCMS m/e (M − H)$^-$ |
|---|---|---|
| 16 | N-piperazinyl-NMe | 452 |
| 17 | tetrahydroisoquinolinyl | 485 |
| 18 | 2-azaspiro[4.5] | 491 |
| 19 | N(n-Pr)$_2$ | 453 |
| 20 | N(Et)(CH$_2$Ph) | 487 |

Example 4

As illustrated in Scheme 4, a suitable 4,7-disubstituted-6-azaindole-3-(2-oxo)acetic acid, as for example the 4,7-dimethoxy-6-azaindole derivative, could be coupled with a 3-piperazinyl-4-substituted-cyclobut-3-ene-1,2-dione, by first preforming the acid chloride using conventional methodology and then performing the coupling step in the presence of a suitable amine base such as diisopropylethylamine. Alternatively, the coupling step could be effected directly with the acid using any of a number of well-known amide coupling reagents, as for example BOP-Cl, together with a suitable amine base such as diisopropylethylamine, in an appropriate solvent such as chloroform.

Compounds D1-D10 were prepared.

D1:

3-[4-[2-[4,7-Dimethoxy-6-azaindol-3-yl]-2-oxoacetyl]piper-azin-1-yl]-4-phenyl-cyclobut-3-ene-1,2-dione To an ice-cold solution of oxalyl chloride (0.025 mL, 0.28 mmol) in dichloromethane (1.5 mL) was added dry DMF (0.020 mL) and solution was stirred at 5° C. for 10 min. The mixture was then cooled at −20° C. and treated dropwise with a solution of 2-(4,7-dimethoxy-6-azaindol-3-yl)-2-oxoacetic acid (0.050 g, 0.20 mmol) in dichoromethane (1 mL). After stirring the mixture at the same temperature for 15 min, a solution of 3-(1-piperazinyl)-4-phenyl-cyclobut-2-ene-1,2-dione (0.048 g, 0.20 mmol) and DIEA (0.070 mL, 0.40 mmol) in dichloromethane (1.5 mL) was added and the reaction mixture was stirred at 5° C. for 1 h. The mixture was then concentrated to half volume, water (2 mL) was added and the remaining volatiles were removed in vacuo. The mixture was further diluted with water (2 mL) and cooled at 0° C. to give a solid. This material was collected by filtration and then purified by preparative HPLC (C-18/10-90% MeCN-5 mmolar aqueous NH$_4$OAc) to give the title compound (0.024 g, 25%) as a white solid:

IR (KBr) 1606 cm$^{-1}$. H$^1$NMR (400 MHz, DMSO-d$_6$) δ 13.23 (br s, 1H), 8.39 (s, 2H), 7.74 (m, 5H), 4.34 (m, 1H), 4.19 (m, 4H), 4.06 (m, 4H), 3.99 (m, 1H), 3.89 (m, 1H), 3.76 (m, 3H). LCMS m/e 475 (M+H)$^+$.

D2:

3-[4-[2-[4,7-Dimethoxy-6-azaindol-3-yl]-2-oxoacetyl]-[2-(R)-methylpiperazin-1-yl]-4-phenyl-cyclobut-3-ene-1,2-dione

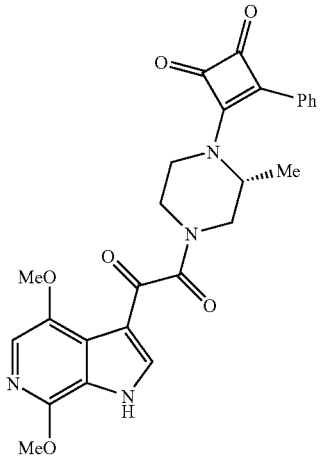

To a suspension of 2-(4,7-dimethoxy-6-azaindol-3-yl)-2-oxoacetic acid (0.050 g, 0.20 mmol) in CHCl$_3$ (2 mL) was added DIEA (0.050 mL, 0.34 mmol), followed by a solution of 3-[2-(R)-methylpiperazin-1-yl]-4-phenyl-cyclobut-2-ene-1,2-dione (0.049 g, 0.20 mmol) and DIEA (0.053 mL, 0.38 mmol) in CHCl$_3$ (2 mL). BOP-Cl was then added in one portion and the reaction mixture was stirred at room temperature for 1.5 h. The mixture was then partitioned with EtOAc—H2O (1:1), the organic phase was separated and the aqueous phase was re-extracted with EtOAc. The combined organic phase was washed (brine), dried (MgSO$_4$) and evaporated to give a solid. This material was purified by preparative HPLC (C-18/10-90% MeCN-5 mmolar aqueous NH$_4$OAc) to give the title compound (0.032 g, 39%) as a white solid:

IR (KBr) 1589 cm$^{-1}$. H$^1$NMR (400 MHz, THF-d$_8$) δ 11.93 (m, 1H), 8.08 (s, 1H), 8.06 (s, 1H), 7.59 (d, J=7.1 Hz, 2H), 7.45 (d, J=7.1 Hz, 2H), 7.38 (t, J=7.1 Hz, 1H), 4.73 (br s, 1H), 4.6-4.4 (m, 1H), 3.99 (s, 3H), 3.86 (s, 1.5H), 3.84 (s, 1.5H), 3.49 (m, 1H), 3.25 (m, 2H), 1.45 (d, J=6.5 Hz, 1.5H), 1.41 (d, J=6.5 Hz, 1.5H). LCMS m/e 489 (M+H)$^+$.

D3:

3-[4-[2-[4,7-Dimethoxy-6-azaindol-3-yl]-2-oxoacetyl]-[3-(R)-methylpiperazin-1-yl]-4-phenyl-cyclobut-3-ene-1,2-dione

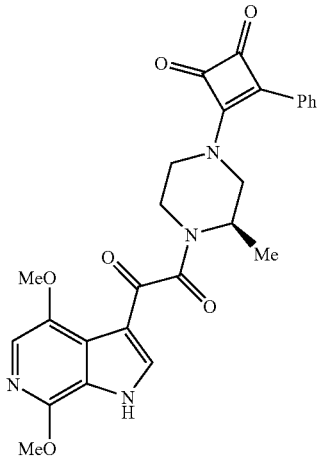

Prepared using a general method as exemplified by the preparation of Compound D1; the title compound is a white solid (27% yield):

IR (KBr) 1607 cm$^{-1}$. H$^1$NMR (400 MHz, DMSO-d$_6$) δ 12.97 (br s, 1H), 8.14 (m, 1H), 8.05 (s, 1H), 7.54 (m, 2H), 7.40 (m, 3H), 4.68 (m, 1H), 4.40 (m, 2H), 3.90 (s, 3H), 3.76 (s, 3H), 3.51 (m, 4H), 1.20 (d, J=6.6 Hz, 1.5H), 1.07 (d, J=6.6 Hz, 1.5H). LCMS m/e 489 (M+H)$^+$.

D4:

Preparation of 3-[4-[2-[4,7-Dimethoxy-6-azaindol-3-yl]-2-oxoacetyl]-[3-(S)-methylpiperazin-1-yl]-4-phenyl-cyclobut-3-ene-1,2-dione

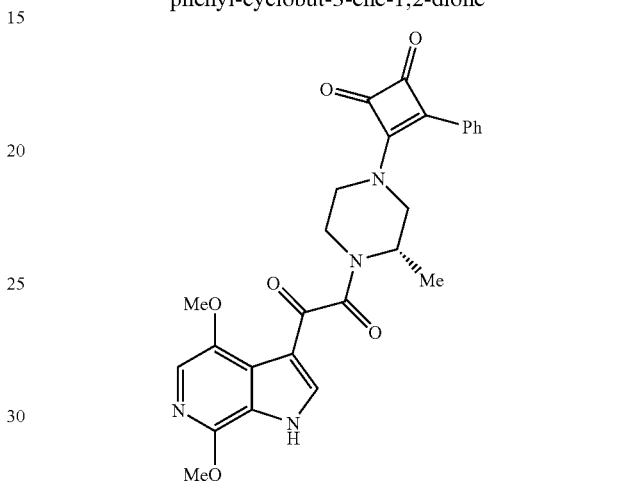

Prepared using a general method as exemplified by the preparation of Compound D1; the title compound is a white solid (32% yield):

IR (KBr) 1607 cm$^{-1}$. H$^1$NMR (400 MHz, DMSO-d$_6$) δ 12.93 (br s, 1H), 8.14 (m, 1H), 8.05 (s, 1H), 7.54 (m, 2H), 7.40 (m, 3H), 4.68 (m, 1H), 4.35 (m, 2H), 3.91 (s, 3H), 3.76 (s, 3H), 3.51 (m, 4H), 1.20 (d, J=7.1 Hz, 1.5H), 1.07 (d, J=7.1 Hz, 1.5H). LCMS m/e 489 (M+H)$^+$.

D5:

3-[4-[2-[4,7-Dimethoxy-6-azaindol-3-yl]-2-oxoacetyl]piper-azin-1-yl]-4-(2-thienyl)-cyclobut-3-ene-1,2-dione

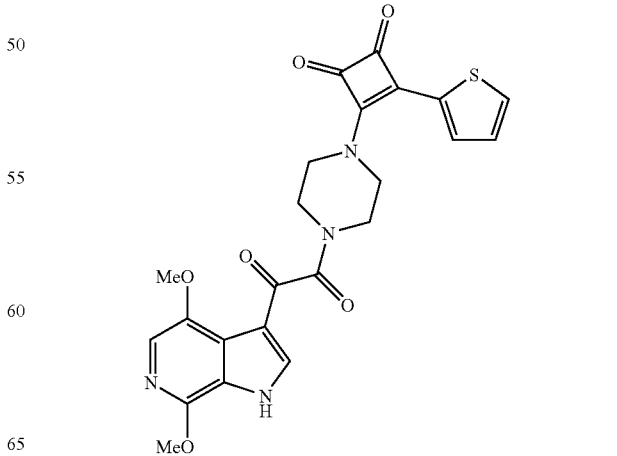

Prepared using a general method as exemplified by the preparation of Compound D1; the title compound is a light yellowish solid (53% yield):

IR (KBr) 1600 cm$^{-1}$. H$^1$NMR (400 MHz, DMSO-d$_6$) δ 13.06 (s, 1H), 8.21 (s, 1H), 7.96 (m, 1H), 7.65 (m, 1H), 7.47 (s, 1H), 7.29 (m, 1H), 4.17 (m, 1H), 3.99 (m, 5H), 3.84 (m, 6H), 3.59 (m, 2H). LCMS m/e 481 (M+H)$^+$.

D6:

3-[4-[2-[4,7-Dimethoxy-6-azaindol-3-yl]-2-oxoacetyl]-[2-(S)-methylpiperazin-1-yl]-4-phenyl-cyclobut-3-ene-1,2-dione

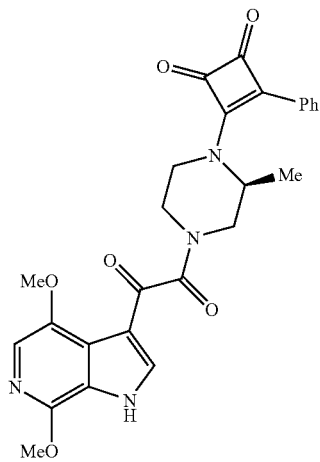

Prepared using a general method as exemplified by the preparation of Compound D2 to give the title compound as a white solid (28% yield):

IR (KBr) 1589 cm$^{-1}$. H$^1$NMR (400 MHz, THF-d$_8$) δ 11.93 (m, 1H), 8.08 (s, 1H), 8.06 (s, 1H), 7.59 (d, J=7.6 Hz, 2H), 7.45 (t, J=7.1 Hz, 2H), 7.38 (d, J=7.6 Hz, 1H), 4.73 (m, 1H), 4.6-4.4 (m, 1H), 3.99 (s, 3H), 3.86 (s, 1.5H), 3.84 (s, 1.5H), 3.69 (m, 2H), 3.49 (m, 1H), 3.25 (m, 2H), 1.45 (d, J=6.5 Hz, 1.5H), 1.41 (d, J=6.5 Hz, 1.5H). LCMS m/e 489 (M+H)$^+$.

D7:

3-[4-[2-[4,7-Dimethoxy-6-azaindol-3-yl]-2-oxoacetyl]piper-azin-1-yl]-4-(2-thiazolyl)-cyclobut-3-ene-1,2-dione

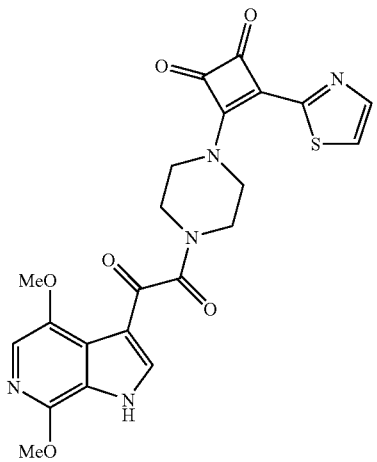

Prepared using a general method as exemplified by the preparation of Compound D2 and purified by preparative TLC (SiO$_2$/DCM-MeOH, 9:1) to give the title compound as a beige solid (12% yield):

IR (KBr) 1608 cm$^{-1}$. H$^1$NMR (400 MHz, DMSO-d$_6$) δ 13.08 (m, 1H), 8.23 (br s, 1H), 7.86 (m, 1H), 7.53 (s, 1H), 7.33 (m, 1H), 4.64 (m, 1H), 4.05 (s, 3H), 3.89 (s, 3H), 3.70 (m, 4H), 3.95 (m, 2H), 3.25 (m, 2H). LCMS m/e 482 (M+H)$^+$.

D8:

3-[4-[2-[4,7-Dimethoxy-6-azaindol-3-yl]-2-oxoacetyl]piper-azin-1-yl]-4-(2-oxazolyl)-cyclobut-3-ene-1,2-dione

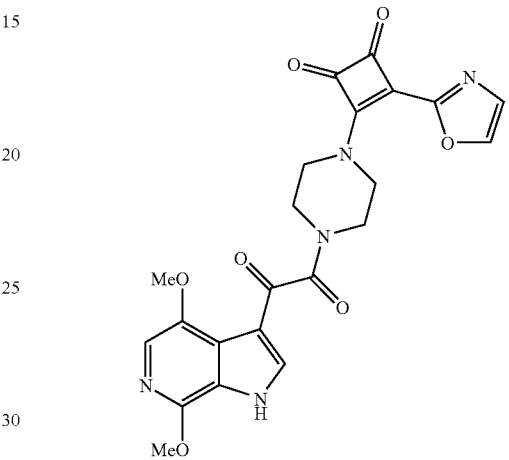

Prepared using a general method as exemplified by the preparation of Compound D2 and purified by preparative HPLC (C-18/10-90% MeCN-5 mmolar aqueous NH$_4$OAc) to give the title compound as a white solid (35% yield):

IR (KBr) 1619 cm$^{-1}$. H$^1$NMR (400 MHz, DMSO-d$_6$) δ 12.99 (br s, 1H), 8.84 (s, 0.5H), 8.80 (s, 0.5H), 8.69 (s, 0.5H), 8.56 (s, 0.5H), 8.13 (d, J=3.6 Hz, 1H), 7.40 (s, 1H), 4.39 (m, 1H), 4.20 (m, 1H), 4.08 (m, 1H), 3.92 (s, 3H), 3.77 (s, 4H), 3.50 (m, 2H), 3.32 (m, 2H). LCMS m/e 466 (M+H)$^+$.

D9:

3-[4-[2-[4,7-Dimethoxy-6-azaindol-3-yl]-2-oxoacetyl]piper-azin-1-yl]-4-(4-fluorophenyl)-cyclobut-3-ene-1,2-dione

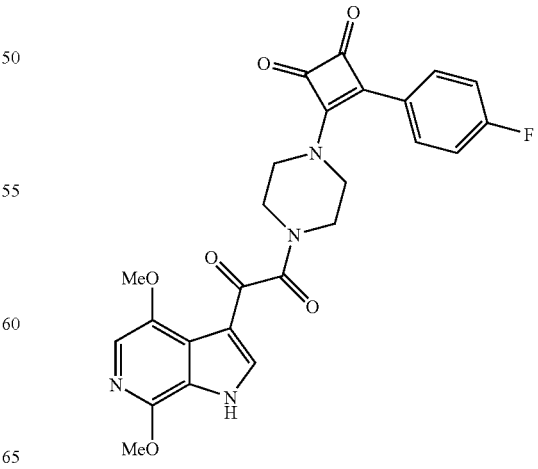

Prepared by first treating 3-(4-tert-butoxycarbonylpiper-azin-1-yl)-4-(4-fluorophenyl)-cyclobut-2-ene-1,2-dione with 4M HCl in dioxane at room temperature to remove the protecting group and then removing the volatiles in vacuo. The resulting material was used according to a general method as exemplified by the preparation of Compound D2 to give the title compound as a white solid (33% yield):

IR (KBr) 1595 cm$^{-1}$. H$^1$NMR (400 MHz, DMSO-d$_6$) δ 13.02 (m, 1H), 8.17 (s, 1H), 7.64 (m, 2H), 7.45 (s, 1H), 7.40 (m, 1H), 7.31 (m, 1H), 4.11 (m, 1H), 3.96 (s, 4H), 3.82 (s, 4H), 3.76 (m, 1H), 3.64 (m, 1H), 3.55 (m, 1H), 3.50 (br s, 2H). LCMS m/e 493 (M+H)$^+$.

D10:

3-[4-[2-[4,7-Dimethoxy-6-azaindol-3-yl]-2-oxoacetyl]piper-azin-1-yl]-4-(3-methoxyphenyl)-cyclobut-3-ene-1,2-dione

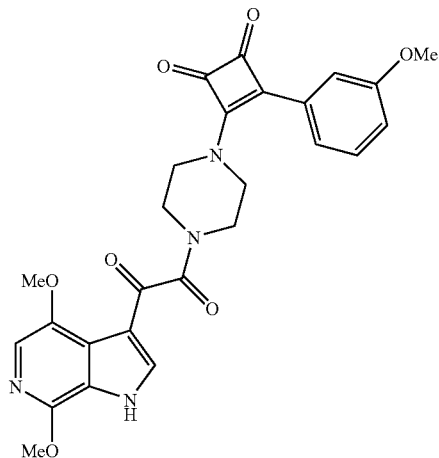

Prepared by first treating 3-(4-tert-butoxycarbonylpiper-azin-1-yl)-4-(3-methoxyphenyl)-cyclobut-2-ene-1,2-dione with 4M HCl in dioxane at room temperature to remove the protecting group and then removing the volatiles in vacuo. The resulting material was used according to a general method as exemplified by the preparation of Compound D2 to give the title compound as a white solid (25% yield);

IR (KBr) 1605 cm$^{-1}$. H$^1$NMR (400 MHz, DMSO-d$_6$) δ 12.98 (m, 1H), 8.16 (br s, 1H), 7.45 (br s, 1H), 7.42 (t, J=8.1 Hz, 1H), 7.10 and 7.07 (ab dd, J=7.5 Hz, 1H), 7.08 (br s, 1H), 7.05 and 6.95 (ab dd, J=7.5 Hz, 1H), 4.11 (m, 1H), 3.96 (br s, 4H), 3.80 (m, 7H), 3.68 (br s, 1H), 3.64 (m, 1H), 3.50 (m, 3H). LCMS m/e 505 (M+H)$^+$.

Example 5

Another variation of 4,7-disubstituted-6-azaindole-3-(2-oxo)acetic acid derivatives is exemplified in Scheme 5. A 7-hydroxy-6-azaindole could be reacted with a suitable halogenating agent, such as POBr$_3$, to give the corresponding 7-halo-6-azaindole. Subsequent Friedel-Crafts type reaction using methyl oxalyl chloride and a suitable catalyst such as AlCl$_3$ in the appropriate solvent, as for example dichloromethane with or without nitromethane as co-solvent, gave a 6-azaindole-3-(2-oxo)acetic acid ester. The latter was saponified to the corresponding 6-azaindole-3-(2-oxo)acetic acid using an alkali metal base, such as K$_2$CO$_3$ or NaOH, in a suitable mixture of a solvent such as methanol or dioxane and water.

The resulting acid was then most conveniently coupled with a 3-piperazinyl-4-substituted-cyclobut-3-ene-1,2-dione using any of a number of well-known amide coupling reagents, as for example BOP-Cl, together with a suitable amine base such as diisopropylethylamine, in an appropriate solvent such as chloroform. The resulting 7-halo-6-azaindole derived intermediate was then coupled with an appropriate coupling partner, as for example an arylstannane, using any of a number of well-known catalyzed cross-coupling methodologies, as for example one using a palladium catalyst in a suitable solvent such as dioxane, to give the desired 7-substituted-6-azaindole derivatives.

Compounds E1-E7 were prepared.

E1:

7-Bromo-4-methoxy-6-azaindole

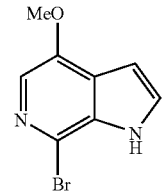

To a flask containing 7-hydroxy-4-methoxy-6-azaindole (0.200 g, 1.22 mmol) was added anisole (3 mL) and then POBr$_3$ (1.57 g, 6.09 mmol). The system was purged with Ar and then it was heated at 160° C. (oil bath temperature) for 1 h. The reaction mixture was then allowed to cool to room temperature, quenched with 2M HBr (5 mL) and extracted with methyl t-butyl ether. The aqueous phase was separated and the pH was adjusted to 6-7, after which it was extracted with EtOAc. The resulting organic phase was dried (MgSO$_4$) and evaporated to give a solid residue which was chromatographed (SiO$_2$/5% MeOH-DCM) to afford the title compound (0.076 g, 27%) as a white solid:

LCMS m/e 227 (M+H)$^+$.

E2:

Methyl 2-(7-bromo-4-methoxy-6-azaindol-3-yl)-2-oxoacetate

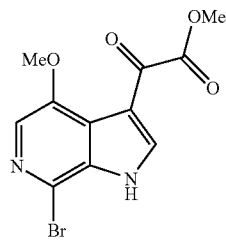

To a solution of AlCl3 (0.587 g, 4.40 mmol) in DCM-MeNO$_2$ (4:1, 3 mL) was added a solution of 7-bromo-4-methoxy-6-azaindole (0.100 g, 0.440 mmol) in DCM-MeNO$_2$ (4:1, 1 mL), followed by methyl oxalyl chloride (0.162 mL, 1.76 mmol). The resulting deep orange solution was stirred at room temperature for 1 h and then it was quenched by the slow addition of 1M NH₄OH. The mixture was extracted with ethyl acetate (2×) and the combined organic phases were dried (MgSO₄) and evaporated to give the title compound (0.136 g, 99%) as a white solid weighing:

¹HNMR (400 MHz, DMSO-d₆) δ 13.16 (s, 1H), 8.41 (d, J=3.0 Hz, 1H), 7.84 (s, 1H), 3.92 (s, 3H), 3.86 (s, 3H). LCMS m/e 313 (M+H)⁺.

E3:

2-(7-Bromo-4-methoxy-6-azaindol-3-yl)-2-oxoacetic acid

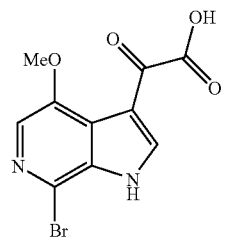

To a solution of methyl 2-(7-bromo-4-methoxy-6-azaindol-3-yl)-2-oxoacetate (0.083 g, 0.265 mmol) in MeOH—H₂O (3:1, 3 mL) was added 1M aqueous K₂CO₃ (1.1 mL, 1.1 mmol). The mixture was stirred at room temperature for 14 h and then it was diluted with H₂O (2 mL). The volatiles were removed under reduced pressure and the remaining solution was acidified to pH 1-2 using 6N HCl. The resulting suspension was cooled at 0° C., the precipitate was filtered and the filtercake was washed with H₂O and then ether. After drying in vacuo, this gave the title compound (0.047 g, 59%) as a light yellow solid:

¹HNMR (400 MHz, DMSO-d₆) δ 13.03 (s, 1H), 8.34 (d, J=3.0 Hz, 1H), 7.82 (s, 1H), 3.91 (s, 3H), 3.46 (br s, 1H). LCMS m/e 299 (M+H)⁺.

E4:

2-(7-Chloro-4-methoxy-6-azaindol-3-yl)-2-oxoacetic acid

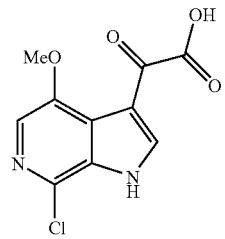

To a solution of 7-chloro-4-methoxy-6-azaindole (0.505 g, 2.77 mmol) in dichloromethane (10 mL) was added via cannula a mixture of AlCl₃ (1.11 g, 8.32 mmol) in dichloromethane (10 mL), followed by methyl oxalyl chloride (0.765 mL, 8.32 mmol). The reaction mixture was stirred at room temperature for 2 days and then it was quenched with 1M NH₄OH and extracted with EtOAc (2×). The combined organic phase was dried (MgSO₄) and evaporated to give 0.360 g of a tan solid. This material was taken up in dioxane (10 mL) and then 0.1N NaOH (26.8 mL, 2.68 mmol) was added. The resulting solution was stirred at room temperature for 2 h and then it was acidified to pH 1 using concentrated HCl. The resulting tan precipitate was filtered, washed with water and dried in vacuo to give the title compound (0.201 g, 25% overall) as a solid:

¹HNMR (400 MHz, DMSO-d₆): 13.91 (br s, 1H), 13.18 (s, 1H), 8.37 (d, J=3.5 Hz, 1H), 7.80 (s, 1H), 3.91 (s, 3H). LCMS m/e 255 (M+H)⁺.

E5:

3-[4-[2-(7-Bromo-4-methoxy-6-azaindol-3-yl)-2-oxoacetyl]pip-erazin-1-yl]-4-phenyl-cyclobut-3-ene-1,2-dione

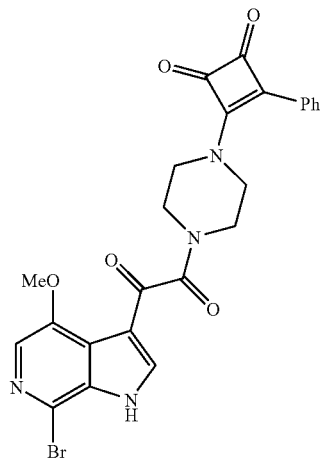

To a solution of 2-(7-bromo-4-methoxy-6-azaindol-3-yl)-2-oxoacetic acid (0.038 g, 0.127 mmol) and DIEA (0.044 mL, 0.254 mmol) in CHCl₃ (1 mL) was added via cannula a solution of 3-(1-piperazinyl)-4-phenyl-cyclobut-2-ene-1,2-dione (0.034 g, 0.140 mmol) and DIEA (0.044 mL, 0.254mmol). BOP-Cl (0.032 g, 0.127 mmol) was then added and the reaction mixture was stirred at room temperature for 4 h. The reaction was quenched with water (15 mL), the organic phase was separated and the aqueous phase was extracted with EtOAc. The combined organic phases were dried (MgSO₄) and evaporated. The resulting residue was taken up in MeOH and purified by preparative HPLC (C-18/10-90% MeCN-5 mmolar aqueous NH4OAc) to give the title compound (0.026 g, 39%) as a yellow solid:

¹HNMR (400 MHz, DMSO-d₆) δ 8.33 (s, 1H), 7.82 (s, 1H), 7.62-7.41 (m, 5H), 4.12 (br s, 1H), 3.97 (br s, 1H), 3.93 (s, 3H), 3.83 (br s, 1H), 3.79 (br s, 1H), 3.67 (br s, 1H), 3.58 (br s, 1H), 3.53 (s, 2H). LCMS m/e 523 (M+H)⁺.

E6:

3-[4-[2-(7-Chloro-4-methoxy-6-azaindol-3-yl)-2-oxoacetyl]piperazin-1-yl]-4-phenyl-cyclobut-3-ene-1,2-dione

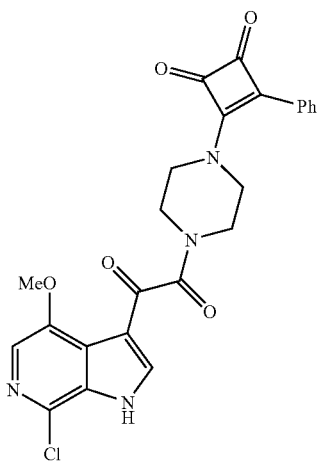

Prepared using a general method as exemplified by the preparation of Compound E5 and purified according to the general method to give the title compound as a yellow solid (20% yield):

$^1$HNMR (400 MHz, DMSO-d$_6$) δ 13.23 (s, 1H), 8.37 (d, J=2.5 Hz, 1H), 7.81 (s, 1H), 7.62-7.41 (m, 5H), 4.12 (br s, 1H), 3.97 (br s, 1H), 3.93 (s, 3H), 3.83 (br s, 1H), 3.79 (br s, 1H), 3.67 (br s, 1H), 3.58 (br s, 1H), 3.53 (s, 2H). LCMS m/e 479 (M+H)$^+$.

E7:

3-[4-[2-[7-(2-Pyrazinyl)-4-methoxy-6-azaindol-3-yl]-2-oxo-acetyl]piperazin-1-yl]-4-phenyl-cyclobut-3-ene-1,2-dione

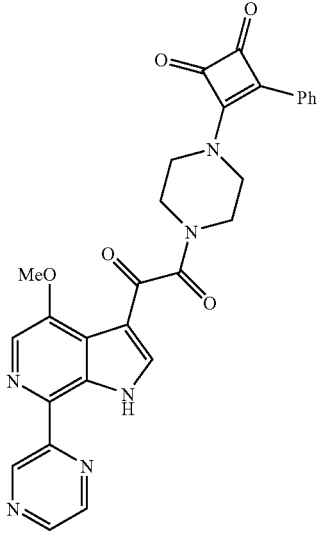

A solution of 3-[4-[2-(7-bromo-4-methoxy-6-azaindol-3-yl)-2-oxoacetyl]piperazin-1-yl]-4-phenyl-cyclobut-3-ene-1,2-dione (0.030 g, 0.057 mmol) and 2-tributylstannylpyrazine (0.025 g, 0.069 mmol) in dioxane (3 mL) was purged with Ar and then Pd(PPh$_3$)$_4$ (0.020 g, 0.017 mmol) was added, the reactor was sealed and the mixture was heated at 90° C. for 16 h. The cooled reaction mixture was diluted with EtOAc, washed (1M aqueous KF, brine), dried (Na$_2$SO$_4$) and evaporated to give a solid. Purification of this material by preparative HPLC (C-18/10-90% MeCN-5 mmolar aqueous NH$_4$OAc) gave the title compound (0.002 g, 7%) as a yellow solid:

$^1$HNMR (DMSO-d$_6$) δ 12.64 (br s, 1H), 9.61 (s, 1H), 8.76 (s, 1H), 8.69 (d, J=2.0 Hz, 1H), 8.26 (s, 1H), 8.24 (s, 1H), 7.64-7.41 (m, 5H), 4.13 (br s, 1H), 4.05 (s, 3H), 3.99 (br s, 1H), 3.87 (br s, 1H), 3.82 (br s, 1H), 3.68 (br s, 1H), 3.62 (br s, 1H), 3.56 (s, 2H). LCMS m/e 523 (M+H)$^+$.

Example 6

Another variation of 4,7-disubstituted-6-azaindole-3-(2-oxo)acetic acid derivatives is exemplified in Scheme 6. A 7-halo-6-azaindole, such as 7-chloro-6-azaindole, was reacted at 100-180° C. under solvent-free conditions with an azole, as for example a triazole or a pyrazole, together with an alkali metal base such as KOH. The resulting 7-substituted-6-azaindole was converted to the corresponding 6-azaindole-3-(2-oxo)acetic acid derivative as previously described for Scheme 5. Similarly, amide coupling of this 6-azaindole-3-(2-oxo)acetic acid derivative with a 3-piperazinyl-4-substituted-cyclobut-3-ene-1,2-dione was accomplished using conditions previously used in Scheme 5.

Compounds F1-F6 were prepared.

F1:

4-Methoxy-7-(1,2,4-triazol-1-yl)-6-azaindole

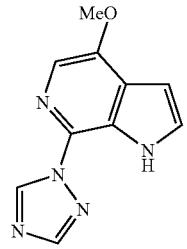

A mixture of 7-chloro-4-methoxy-6-azaindole (1.029 g, 5.62 mmol), 1,2,4-triazole (11.6 g, 30 equiv), copper bronze (0.72 g, 11.2 mgatom) and finely pulverized KOH (0.63 g, 11.2 mmol) was heated in a sealed tube at 160° C. (oil bath temperature) for 18 h. The cooled mixture was taken up in MeOH and the resulting slurry was filtered through a pad of Celite. The filtrate was evaporated, the residue taken up in EtOAc and the resulting suspension was filtered. This process was repeated and the resulting solution was susequently adsorbed on silica gel and the volatiles were removed in vacuo. This solid was applied to the top of a silica gel chromatography column, which was eluted with 10-50% EtOAc—CH$_2$Cl$_2$ to give the title compound (0.697 g, 58%) as an off-white solid:

$^1$Hnmr (400 MHz, CDCl$_3$) δ 10.23 (s, 1H), 9.23 (s, 1H), 8.16 (s, 1H), 7.59 (s, 1H 7.40 (dd, J=2.2, 3.1, 1H), 6.74 (dd, J=2.2, 3.1, 1H), 4.06 (s, 3H). LCMS m/e 216 (M+H)$^+$.

F2:

4-Methoxy-7-(1,2,4-triazol-1-yl)-6-azaindol-3-yl-oxoacetic acid

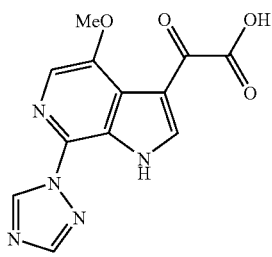

To a mixture of AlCl₃ (0.665 g, 5.0 mmol) in 4 mL of CH₂Cl₂-MeNO₂ (4:1) was added 4-methoxy-7-(1,2,4-triazol-1-yl)-6-azaindole (0.108 g, 0.50 mmol) as a solid. To the resulting solution was added methyl oxalyl chloride (0.185 mL, 2.0 mmol) dropwise and then the mixture was stirred at room temperature for 16 h. The reaction mixture was then carefully poured into 20% aqueous ammonium acetate and EtOAc were added. The resulting emulsion was filtered and the residue was washed with additional EtOAc. The organic phase was washed (brine), dried (Na₂SO₄) and evaporated, and the residue was triturated with MeOH to give 4-methoxy-7-(1,2,4-triazol-1-yl)-6-azaindol-3-yl-oxoacetic acid methyl ester (0.069 g, 46%) as a yellow solid: MS m/e 300 (M−H)⁻. This material (0.069 g, 0.229 mmol) was taken up in 3 mL of MeOH, 1M K₂CO₃ (0.9 mL, 0.9 mmol) was added and the mixture was stirred at room temperature for 20 h. The solution was then diluted with an equal volume of water and concentrated in vacuo. The resulting aqueous solution was cooled at 0° C. and acidified to pH 1-2 with 6N HCl. This gave a bright yellow precipitate which was filtered, washed with cold 0.1N HCl and then with ether. The wet solid was suspended in ether with sonication and then it was filtered and dried in vacuo to give the title compound (0.049 g, 75%) as a yellow powder:

¹Hnmr (400 MHz, DMSO-d₆) δ 12.53 (s, 1H), 9.42 (s, 1H), 8.47 (s, 1H), 8.28 (s, 1H) 7.91 (s, 1H), 3.99 (s, 3H). LCMS m/e 286 (M−H)⁻.

F3:

4-Methoxy-7-(3-methyl-pyrazol-1-yl)-6-azaindole

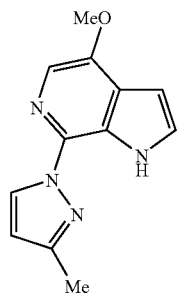

Prepared using a general method as exemplified by preparation of Compound F2 to give the title compound as a cream-coloured solid (46% yield):

¹Hnmr (400 MHz, CDCl₃) δ 10.66 (br s, 1H), 8.55 (s, 1H), 7.57 (s, 1H), 7.41 (dd, J=3.2, 2.3 Hz, 1H), 6.71 (dd, J=3.2, 2.3 Hz, 1H), 6.30 (d, J=2.5 Hz, 1H), 4.06 (s, 3H), 2.45 (s, 3H). LCMS m/e 229 (M+H)⁺.

F4:

4-Methoxy-7-(3-methyl-pyrazol-1-yl)-6-azaindol-3-yl-oxo-acetic acid

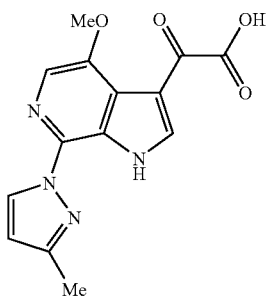

Prepared using a general method as exemplified by the preparation of Compound F2 to give the title compound as a cream coloured solid (25% yield):

¹Hnmr (400 MHz, DMSO) δ 12.33 (s, 1H), 8.57 (s, 1H), 8.29 (s, 1H), 7.85 (s, 1H), 6.47 (s, 1H), 3.98 (s, 3H), 2.54 (s, 3H). LCMS m/e 301 (M+H)⁺.

F5:

3-[4-[2-[7-(1,2,4-Triazol-1-yl)-4-methoxy-6-azaindol-3-yl]-2-oxoacetyl]piperazin-1-yl]-4-phenyl-cyclobut-3-ene-1,2-dione

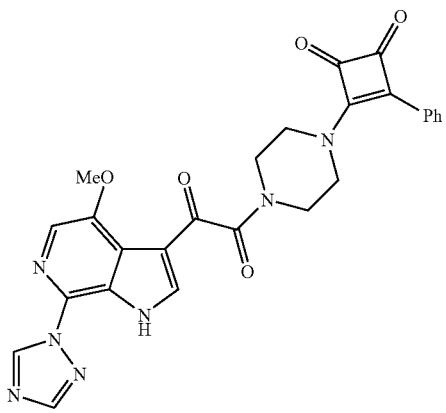

To a suspension of 4-methoxy-7-(1,2,4-triazol-1-yl)-6-azaindol-3-yl-oxoacetic acid (0.024 g, 0.084 mmol) and 3-(1-piperazinyl)-4-phenyl-cyclobut-2-ene-1,2-dione (0.019 g, 0.08 mmol) in CHCl₃ (3 mL) was added DIEA (0.014 mL, 0.08 mmol), followed by BOP-Cl (0.020 g, 0.08 mmol). The mixture was stirred at room temperature for 2.5 h and then it was partitioned with EtOAc-10% saturated NaHCO₃. The organic phase was separated, dried (Na₂SO₄) and evaporated to give a cream-coloured solid. This material was triturated with MeOH-MeCN (1:1) and the resulting solid was filtered and dried in vacuo to give the title compound (0.011 g, 27%) as an off-white solid:

$^1$Hnmr (400 MHz, DMSO-d$_6$) δ 12.61 (br s, 1H), 9.43 (s, 1H), 8.47 (s, 1H), 8.25 (s, 1H), 7.93 (s, 1H), 7.65-7.43 (m, 5H), 4.14 (br s, 1H), 4.02 (s, 3H), 3.88 (br s, 1H), 3.83 (br s, 1H), 3.69 (br s, 1H), 3.63 (br s, 1H), 3.58 (br s, 1H), 3.33 (br s, 2H). LCMS m/e 512 (M+H)$^+$.

F6:

3-[4-[2-[7-(3-Methyl-pyrazol-1-yl)-4-methoxy-6-azaindol-3-yl]-2-oxoacetyl]piperazin-1-yl]-4-phenyl-cyclobut-3-ene-1,2-dione

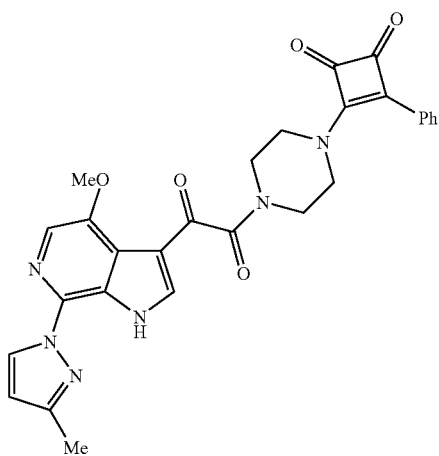

To a suspension of 4-methoxy-7-(3-methyl-pyrazol-1-yl)-6-azaindol-3-yl-oxoacetic acid (0.030 g, 0.10 mmol) and 3-(1-piperazinyl)-4-phenyl-cyclobut-2-ene-1,2-dione (0.029 g, 0.12 mmol) in CHCl$_3$ (3 mL) was added DIEA (0.042 mL, 0.24 mmol), followed by BOP-Cl (0.026 g, 0.10 mmol). The mixture was stirred at room temperature for 2.5 h and then it was evaporated to dryness. The residue was purified by preparative HPLC (C-18/10-90% MeCN-5 mmolar aqueous NH$_4$OAc) to give impure material. Repurification using preparative HPLC (C-18/10-90% MeCN-0.1% aqueous TFA) afforded the TFA salt of the title compound (0.0064 g, 10%) as a pale yellow solid:

$^1$Hnmr (400 MHz, DMSO-d$_6$) δ 12.34 (br s, 1H), 8.54 (s, 1H), 8.23 (s, 1H), 7.83 (s, 1H), 7.63-7.40 (m, 5H), 6.44 (d, J=2.7 Hz, 1H), 4.14 (br s, 1H), 4.02 (br s, 1H), 3.97 (s, 3H), 3.88 (br s, 1H), 3.83 (br s, 1H), 3.68 (br s, 1H), 3.64 (br s, 1H), 3.57 (br s, 2H), 2.42 (s, 3H). LCMS m/e 525 (M+H)$^+$.

Biology

"μM" means micromolar;
"mL" means milliliter;
"μl" means microliter;
"mg" means milligram;

The materials and experimental procedures used to obtain the results reported in Tables 3-4 are described below.

Cells:

Virus production—Human embryonic Kidney cell line, 293T, was propagated in Dulbecco's Modified Eagle Medium (Invitrogen, Carlsbad, Calif.) containing 10% fetal Bovine serum (FBS, Sigma, St. Louis, Mo.).

Virus infection—Human epithelial cell line, HeLa, expressing the HIV-1 receptor CD4 was propagated in Dulbecco's Modified Eagle Medium (Invitrogen, Carlsbad, Calif.) containing 10% fetal Bovine serum (FBS, Sigma, St. Louis, Mo.) and supplemented with 0.2 mg/mL Geneticin (Invitrogen, Carlsbad, Calif.).

Virus—Single-round infectious reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen et al, Ref. 41). Transfections were performed using lipofectAMINE PLUS reagent as described by the manufacturer (Invitrogen, Carlsbad, Calif.).

Experiment

1. HeLa CD4 cells were plated in 96 well plates at a cell density of 1×10$^4$ cells per well in 100 μl Dulbecco's Modified Eagle Medium containing 10% fetal Bovine serum and incubated overnight.
2. Compound was added in a 2 μl dimethylsulfoxide solution, so that the final assay concentration would be ≦10 μM.
3. 100 μl of single-round infectious reporter virus in Dulbecco's Modified Eagle Medium was then added to the plated cells and compound at an approximate multiplicity of infection (MOI) of 0.01, resulting in a final volume of 200 μl per well.
4. Virally-infected cells were incubated at 37 degrees Celsius, in a CO$_2$ incubator, and harvested 72 h after infection.
5. Viral infection was monitored by measuring luciferase expression from viral DNA in the infected cells using a luciferase reporter gene assay kit, as described by the manufacturer (Roche Molecular Biochemicals, Indianapolis, Ind.). Infected cell supernatants were removed and 50 μl of lysis buffer was added per well. After 15 minutes, 50 μl of freshly-reconstituted luciferase assay reagent was added per well. Luciferase activity was then quantified by measuring luminescence using a Wallac microbeta scintillation counter.
6. The percent inhibition for each compound was calculated by quantifying the level of luciferase expression in cells infected in the presence of each compound as a percentage of that observed for cells infected in the absence of compound and subtracting such a determined value from 100.
7. An EC$_{50}$ provides a method for comparing the antiviral potency of the compounds of this disclosure. The effective concentration for fifty percent inhibition (EC$_{50}$) was calculated with the Microsoft Excel Xlfit curve fitting software. For each compound, curves were generated from percent inhibition calculated at 10 different concentrations by using a four parameter logistic model (model 205).

TABLE 3

| Biological Data Key for EC$_{50}$s | | |
|---|---|---|
| Compounds with EC$_{50}$s >5 μM | Compounds with EC$_{50}$s <5 μM and >0.5 μM | Compounds with EC$_{50}$ <=0.5 μM and ≧0.050 μM |
| Group C | Group B | Group A |

The EC$_{50}$ data for the compounds is shown in Table 4.
Results
TABLE 4
| Number | Structure | EC$_{50}$ μM |
|---|---|---|
| 1 | 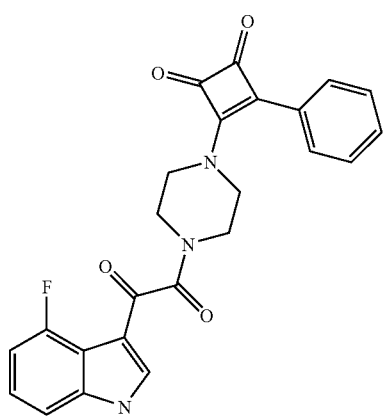 | A |
| 2 | 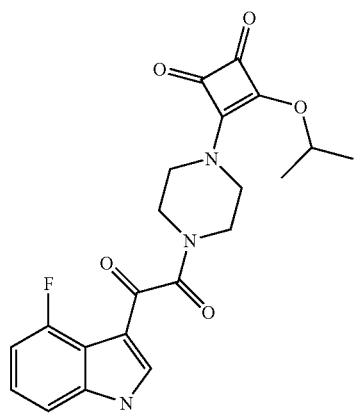 | A |
| 3 | 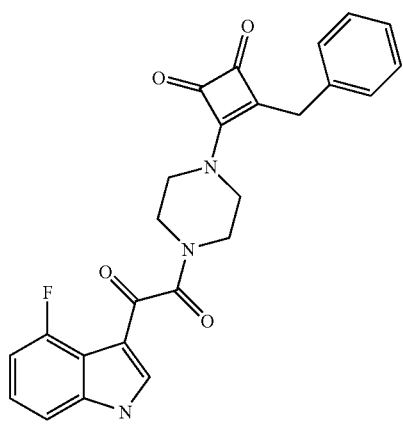 | C |
TABLE 4-continued
| Number | Structure | EC$_{50}$ μM |
|---|---|---|
| 4 | 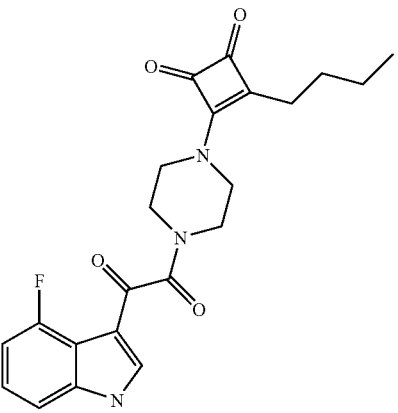 | C |
| 5 | 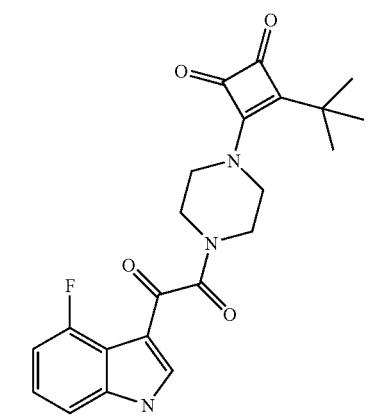 | B |
| 6 | 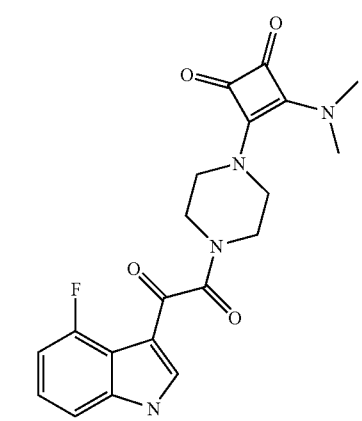 | B |

TABLE 4-continued

| Number | Structure | EC$_{50}$ µM |
|---|---|---|
| 7 | 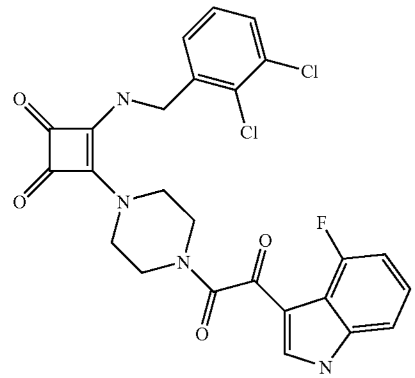 | C |
| 8 | 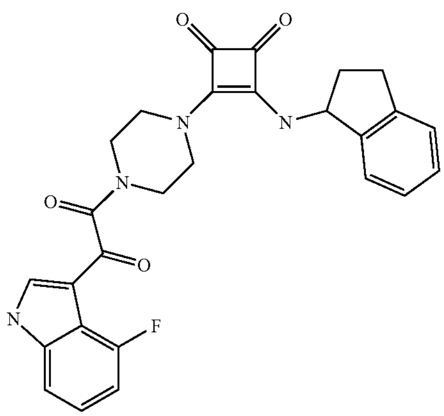 | C |
| 9 | 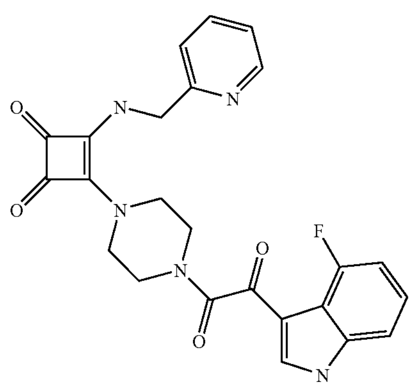 | C |
| 10 | 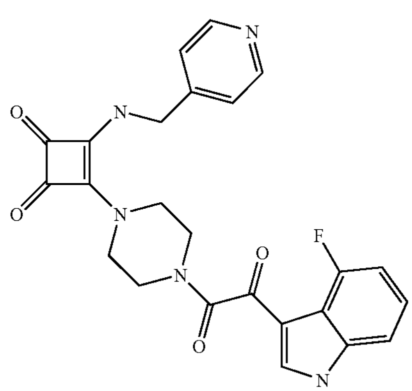 | C |
| 11 | | C |
| 12 | | C |
| 13 | | C |
| 14 | | C |

TABLE 4-continued

| Number | Structure | EC$_{50}$ μM |
|---|---|---|
| 15 | 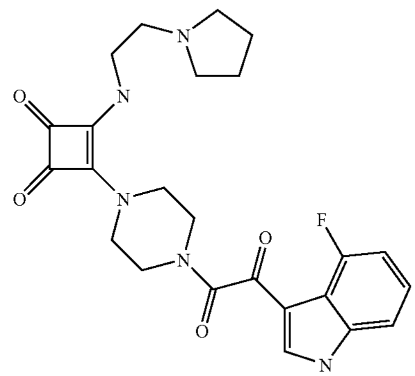 | C |
| 16 | 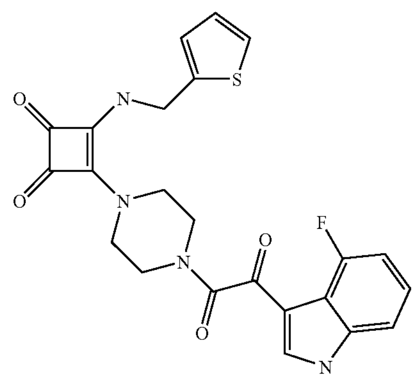 | C |
| 17 | 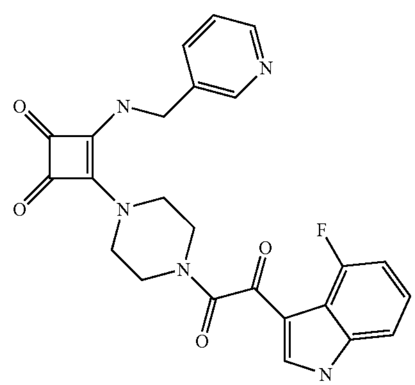 | C |
| 18 | 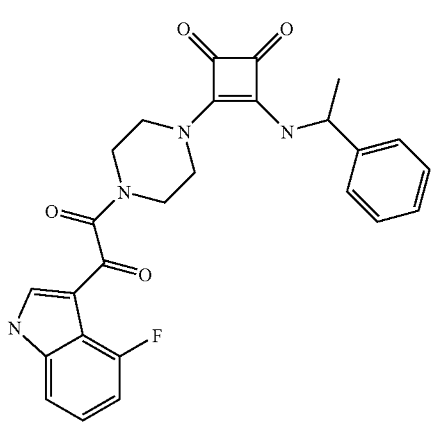 | C |
| 19 | | C |
| 20 | | C |
| 21 | | C |
| 22 | | C |

TABLE 4-continued
| Number | Structure | EC$_{50}$ μM |
|---|---|---|
| 23 | 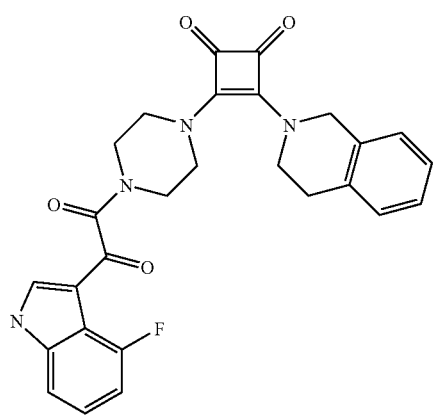 | C |
| 24 | 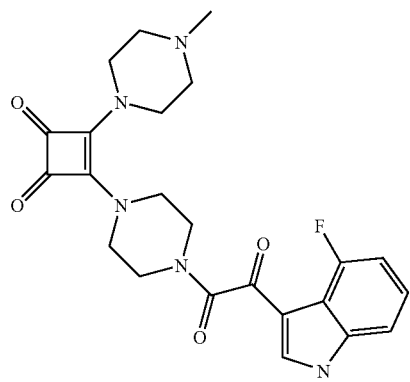 | C |
| 25 | 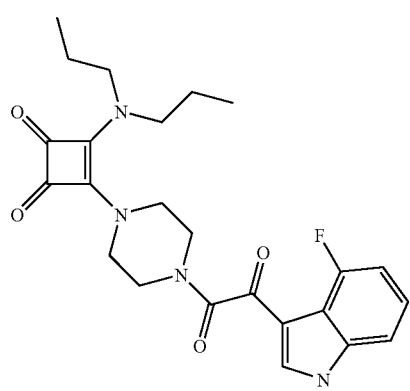 | C |
TABLE 4-continued
| Number | Structure | EC$_{50}$ μM |
|---|---|---|
| 26 | 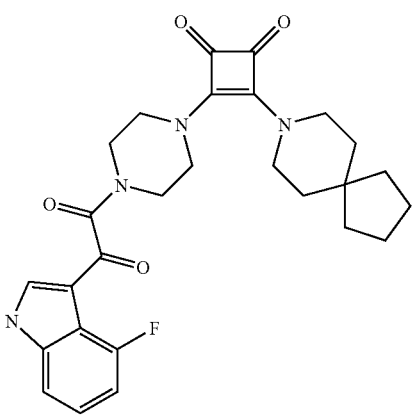 | C |
| 27 | 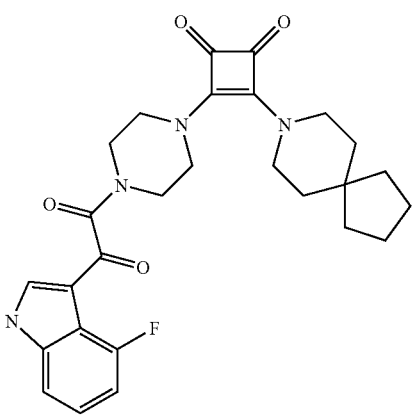 | A |
| 28 | 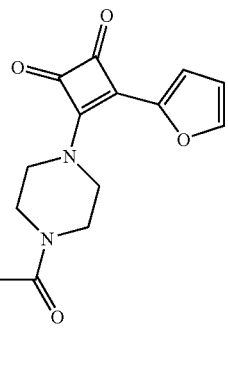 | B |

TABLE 4-continued
| Number | Structure | EC$_{50}$ μM |
|---|---|---|
| 29 | 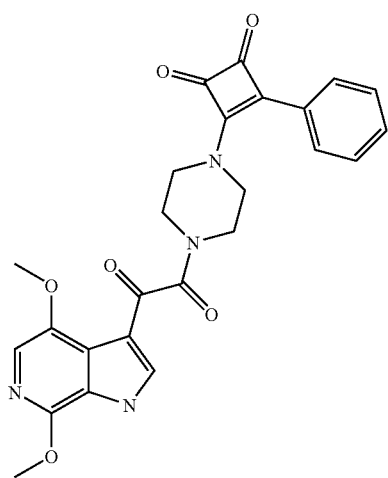 | A |
| 30 | 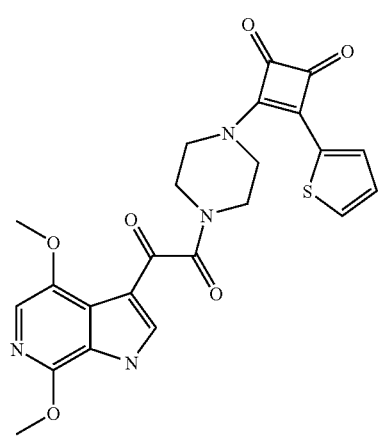 | A |
| 31 | 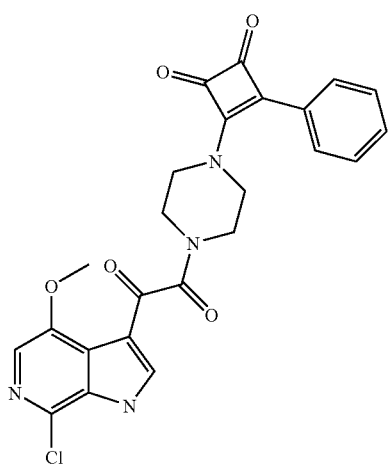 | A |
| 32 | 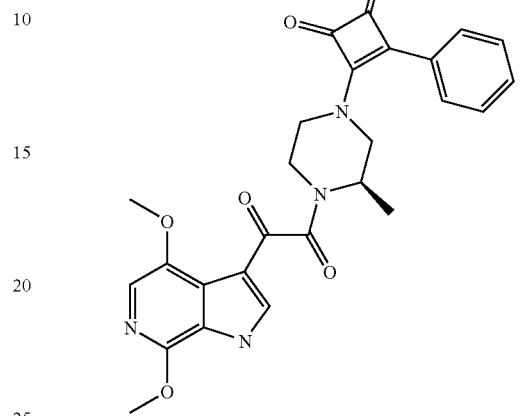 Chiral | A |
| 33 | 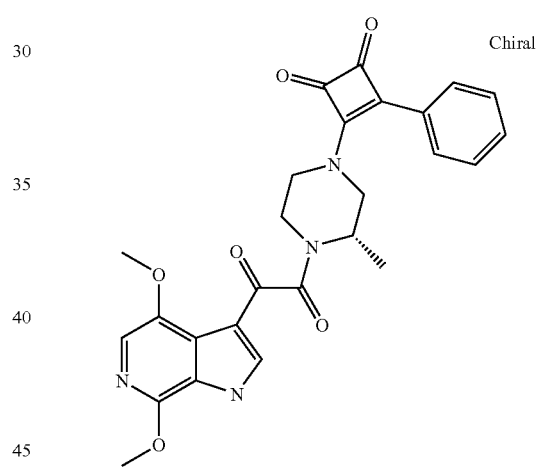 Chiral | A |
| 34 | 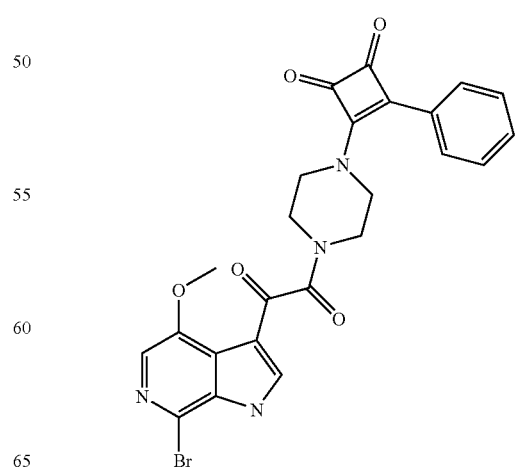 | A |

TABLE 4-continued

| Number | Structure | EC$_{50}$ μM |
|---|---|---|
| 35 | 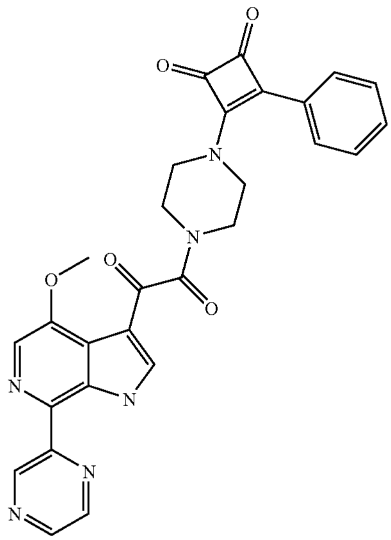 | A |
| 36 | 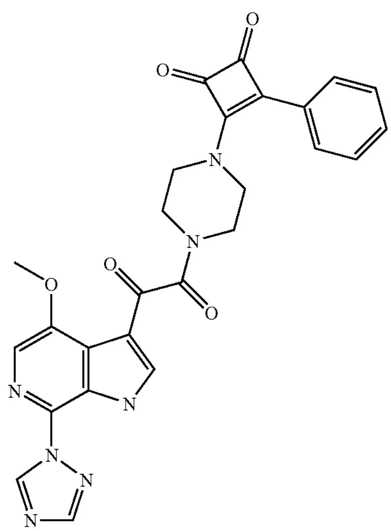 | A |
| 37 | 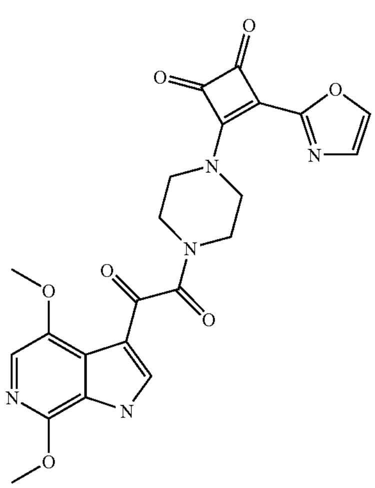 | B |
| 38 | (Chiral) | A |
| 39 | (Chiral) | A |
| 40 | | A |

TABLE 4-continued

| Number | Structure | EC$_{50}$ μM |
|---|---|---|
| 41 | 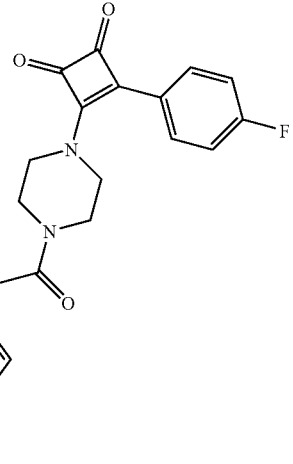 | A |
| 42 | 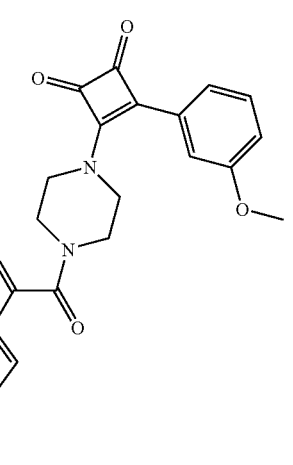 | A |
| 43 | 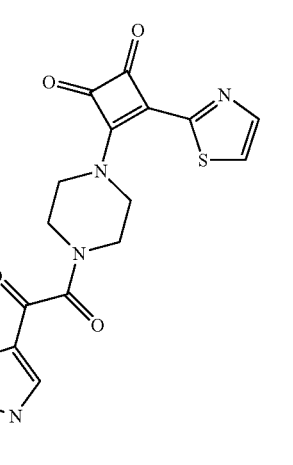 | B |

What is claimed is:

1. A compound of Formula I, or pharmaceutically acceptable salts thereof,

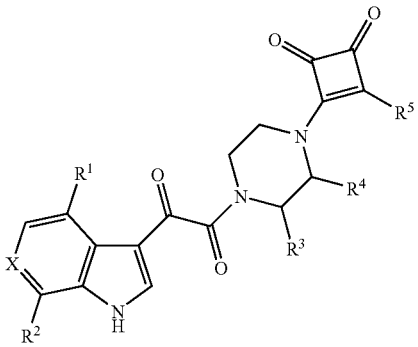

wherein: X is CH or N;

R$^1$ is F or methoxy;

R$^2$ is methoxy, Cl, Br, or heteroaryl wherein said heteroaryl is optionally substituted with one or two of the same or different members selected from the group consisting of amino, nitro, cyano, hydroxy, C$_{1-6}$ alkoxy, —C(O)NH$_2$, C$_{1-6}$ alkyl, —NHC(O)CH$_3$, halogen, and trifluoromethyl;

R$^3$ is H or methyl;

R$^4$ is H or methyl;

R$^5$ is alkyl, aryl, heteroaryl, OR$^6$, or NR$^6$R$^7$;

R$^6$ and R$^7$ are each independently selected from the group consisting of H, C$_1$-C$_6$ alkyl and C$_3$-C$_6$ cycloalkyl, wherein said C$_3$-C$_6$ cycloalkyl can fuse with phenyl or pyridine; R$^6$ and R$^7$ can optionally be joined by C, O, N or S atom, among which the junctioning C and N atom can be substituted with C$_1$-C$_6$ alkyl, C$_3$-C$_6$ cycloalkyl group or junctioning C atom can be a part of C$_3$-C$_6$ cycloalkyl group.

2. A compound of claim 1 in which

R$^5$ is phenyl or thienyl;

R$^2$ is hydrogen, methoxy, chloro, bromo, pyrazinyl, triazolyl, or pyrazolyl.

3. A pharmaceutical composition which comprises an antiviral effective amount of a compound of Formula I, including pharmaceutically acceptable salts thereof, as claimed in claim 1, and one or more pharmaceutically acceptable carriers, excipients or diluents.

4. The composition of claim 3 further comprising a second compound having anti-HIV activity.

5. The pharmaceutical composition of claim 3, useful for treating infection by HIV, which additionally comprises an antiviral effective amount of an AIDS treatment agent selected from the group consisting of:

(a) an AIDS antiviral agent;

(b) an anti-infective agent;

(c) an immunomodulator; and (d) HIV entry inhibitors.

6. A method for treating a mammal infected with HIV comprising administering to said mammal an antiviral effective amount of a compound of Formula I, including pharmaceutically acceptable salts thereof, as claimed in claim 1, and one or more pharmaceutically acceptable carriers, excipients or diluents.

7. The method of claim 6 comprising administering to said mammal an antiviral effective amount of a compound of Formula I in combination with an antiviral effective amount of an AIDS treatment agent selected from the group consisting of: an AIDS antiviral agent; an anti-infective agent; an immunomodulator; and an HIV entry inhibitor.

* * * * *